United States Patent [19]

Kun et al.

[11] Patent Number: 6,017,958
[45] Date of Patent: *Jan. 25, 2000

[54] METHOD OF TREATING MALIGNANT TUMORS WITH THYROXINE ANALOGUES HAVING NO SIGNIFICANT HORMONAL ACTIVITY

[75] Inventors: Ernest Kun, Mill Valley; Jerome Mendeleyev, Tiburon, both of Calif.

[73] Assignee: Octamer, Inc., Berkeley, Calif.

[*] Notice: This patent is subject to a terminal disclaimer.

[21] Appl. No.: 08/833,272

[22] Filed: Apr. 3, 1997

Related U.S. Application Data

[63] Continuation-in-part of application No. 08/655,267, Jun. 4, 1996, Pat. No. 5,736,576.

[51] Int. Cl.⁷ .......................... A61K 31/235; A61K 31/24
[52] U.S. Cl. .......................... 514/532; 514/535; 514/543
[58] Field of Search .................................. 514/532, 535, 514/543

[56] References Cited

U.S. PATENT DOCUMENTS

| | | | |
|---|---|---|---|
| 4,724,234 | 2/1988 | Cone, Jr. ................................. | 514/728 |
| 4,816,255 | 3/1989 | Ghent et al. ............................. | 424/150 |
| 5,736,576 | 4/1998 | Kun et al. ............................... | 514/570 |

FOREIGN PATENT DOCUMENTS

| | | |
|---|---|---|
| 642159 | 8/1950 | United Kingdom . |
| 643089 | 9/1950 | United Kingdom . |
| WO 93/2444 A1 | 12/1993 | WIPO . |

OTHER PUBLICATIONS

Chen, et al., "A Novel Thyroid Hormone Analog Binds to Tubulin and Induces Apoptosis and Mitotic Arrest in Human Cancer Cells," *FASEB*—Abstract (1997).
Bauer et al., "Modification of Growth Related Enzymatic Pathways and Apparent Loss of Tumorigenicity of a Ras-Transformed Bovine Endothelial Cell Line by Treatment with 5–Iodo–6–Amino–1, 2–Benzopyrone (INH₂BP)," *International J. of Oncology* 8:239–252 (1996).
Borrows et al., "The Synthesis of Thyroxine and Related Substances. Part I. The Preparation of Tyrosine and Some of its Derivatives, and a New Route to Thyroxine," *J. Chem. Soc.* 1949 (Supp. Issue No. 1):S185–S190 (1949).
Borrows et al., "The Synthesis of Thyroxine and Related Substances. Part II. Preparation of Dinitrophenyl Ethers," *J. Chem. Soc.* 1949 (Supp. Issue No. 1):S190–S199 (1949).
Borrows et al., "Synthesis of Thyroxine and Realted Substances. I. The Preparation of Tyrosine and Some of its Derivatives and a New Route to Thyroxine," *Chem. Abstr.* 44:574h (1950).
Borrows et al., Diphenyl Ethers, *Chem. Abstr.* 45:P7594b (1951).
Burton, et al., "Traction forces of cytokinesis measured with optically modified elastic substrate," *Nature* 385:450–454 (1997).
Clayton et al., "The Synthesis of Thyroxine and Related Substances. Part VIII. The Preparation of Some Halogeno– and Nitro–diphenyl Ethers," *J. Am. Chem. Soc.* 1951:2467–2473 (1951).
Clayton et al., "Synthesis of Thyroxine and Realted Substances. VIII. The Preparation of Some Halo– and Nitrodiphenyl Ethers," *Chem. Abstr.* 46:8056g (1952).
Cole, et al., "Inhibition of HIV–1 IIIb Replication in AA–2 Cells in Culture by Two Ligands of Poly (ADP–Ribose) Polymerase: 6–Amino–1, 2–benzopyrone and 5–iodo–6–amino–1, 2–benzopyrone," *Biochem Biophys. Res. Commun.* 180:504–514 (1991).
Crowder et al., "Bisbenzylisoquinolines," *Chem. Abstr.* 52:17163d (1958).
Crowder et al., "Bisbenzylisoquinolines. Part II. The Synthesis of 5–(2–Aminoethyl)–4'–carboxy–2,3–dimethoxydiphenyl Ether," *J. Chem. Soc.* 1958:2142–2149 (1958).
Dunphy, "The Decision to Enter Mitosis," *Trends Cell. Biol.* 4:202–207 (1994).
Dykes et al., "Response of Human Tumor Xenografts in Athymic Nude Mice to Docetaxel," *BIOSIS* 95:487870 (1995).
Gemmill et al., "3–Iodo–, 3, 3'–Diiodo– and 3, 3'–Diiodo–5–Bromthyroxine," *J. Am. Chem. Soc.* 78:2434–2436, (1956).
Grinberg et al., "Studies with Mouse Pituitary Thyrotropic Tumors. V. Effect of Various Thyroxine Analogs on Growth and Secretion," *Chem. Abstr.* 57:14335d (1962).
Grinberg et al., "Studies with Mouse Pituitary Thyrotropic Tumors. V. Effect of Various Thyroxine Analogs on Growth and Secretion," *Cancer Research* 22:835–841 (1962).
Grutzmeier, S., "Myxoedema in a Case of Acute Myeloid Leukemia," *EMBASE* 85:118288 (1985).
Jorgensen, "Thyroid Hormones and Analogues, I. Synthesis, Physical Properties and Theoretical Calculations," In: *Hormonal Proteins and Peptides* VI:57–105, C.H. Li, Ed., Academic Press, NY (1978).
Jorgensen, "Thryoid Hormones and Analogues. II. Structure–Activity Relationships," In: *Hormonal Proteins and Peptides*, VI:107–204, C.H. Li, Ed., Academic Press, NY (1978).
Kawabe et al., "HOXII Interacts with Protein Phosphatase PP2a and PP1 and Disrupts G2/M Cell Cycle Checkpoint," *Nature* 385:454–458 (1997).

(List continued on next page.)

*Primary Examiner*—Jerome D. Goldberg
*Attorney, Agent, or Firm*—Albert P. Halluin; Howrey & Simon

[57] ABSTRACT

The present invention provides methods for treating cancer, particularly malignant tumors, with thyroxine analogues having no significant hormonal activity. A thyroxine analogue is administered to an afflicted mammal in an amount effective to cause depression or regression of malignant tumor growth or to treat cancer. Particularly preferred thyroxine analogues are those capable of causing about 35 percent or more inhibition of initial velocity of microtubule protein assembly in vitro.

6 Claims, 15 Drawing Sheets

OTHER PUBLICATIONS

Kumaoka et al., "The Effect of Thyroxine analogs on a Transplantable–Mouse Pituitary Tumor," *Chem. Abstr.* 54:18779i (1960).

Kumaoka et al., "The Effect of Thyroxine Analogues on a Transplantable Mouse Pituitary Tumor," *Endocrinology* 66:32–38 (1960).

Kun et al., "Induction of Tumor Apotosis by methyl–3, 5–diiodo–4–(4'–methoxyphenoxy) benzoate (DIME)", Abstract No. 102, *Int. J. Oncol.* 9:supplement 829 (1996).

Masuda et al., "Triiodothyroformic Acid. Synthesis of Triidothyroformic Acid and its Derivatives," *Takeda Kenkyusho Ho* 29(4):545–552 (in Japanese) (1970).

Masuda et al., "Thyroxine Related Compounds. I. Synthesis of Triiodothyroformic Acid and its Derivatives," *Chem. Abstr.* 75:40431q (1971).

Meltzer et al., "Thyroxine Analogs," *J. Org. Chem.* 22:1577–1581 (1957).

Meltzer et al., "Thyroxine Analogs," *Chem. Abstr.* 52:7210d (1958).

Mendeleyev et al., "Structural Specificity and Tumoricidal Action of Methyl–3, 5–Diiodo–4–(4'–Methoxyphenoxy) Benzoate (DIME)," *Intl. J. Oncol.* 10:689–695 (1997).

Mitchison et al., "Microtubule Assembly Nucleated by Isolated Centrosomes," *Nature* 312:232–237 (1984).

Money et al., "The Effect of Changes in Chemical Structure of Some Thyroxine Analogs on the Metamorphosis of Rana Piplens Tadpoles," *Chem. Abstr.* 52:20701a (1958).

Money et al., "The Effect of Change in Chemical Structure of Some Thyroxine Analogues on the Metamorphosis of *Rana Pipiens* Tadpoles," *Endocrinology* 63:20–28 (1958).

Money et al., "Effect of Various Thyroxine Analogs on Suppression of Iodine–131 Uptake by the Rat Thyroid," *Chem. Abstr.* 53:14327i (1959).

Money et al., "The Effect of Various Thyroxine Analogues on Suppression of Iodine–131 Uptake by the Rat Thyroid[1]," *Endocrinology* 64:123–125 (1959).

Osbourne et al., "Effect of Estrogens and Antiestrogens on Growth of Human Breast Cancer Cells in Athymic Nude Mice," *Cancer Res.* 45:584–590 (1985).

Ozzello & Sordat, "Behaviour of Tumors Produced by Transplantation of Human Mammary Cell Lines in Athymic Nude Mice," *Eur. J. Cancer* 16:553–559 (1980).

Pinkel et al., "Cytogentic Analysis Using Quantitative High– Sensitivity Fluorescence Hybridization," *Proc. Natl. Acad. Sci. U.S.A.* 83:2934–2938 (1986).

Siebert et al., "Clonal Variation of MCF–7 Breast Cancer Cells in Vitro and in Athymic Nude Mice," *Cancer Res.* 43:2223–2239 (1983).

Smythe et al., "Coupling of Mitosis to the Completion of S Phase in Xenopus Occurs via Modulation of the Tyrosine Kinase that Phosphorylates $P34^{cdc2}$," *Cell* 68:787–797 (1992).

Stasilli et al., "Analogs in Rats," *Chem. Abstr.* 53:14327ci (1959).

Stasilli et al., "Antigoitrogenic and Calorigenic Activities of Thyroxine Analogues in Rats," *Endocrinology* 64:62–82 (1959).

Tiwari, et al., "A pH and temperature–dependent cycling method that doubles the yield of microtubule protein," *Anal. Biochem.* 215:96–103 (1993).

Tomita et al., "Synthesis and Biological Activity of Some Triiodinated Analogues of Thyroxine," *J. Biol. Chem.* 219:595–604 (1956).

Usui et al., "Phosphoportein Phosphatases in Human Erythrocyte Cytosol," *J. Biol. Chem.* 258:10455–10463 (1983).

Vidair et al., "Evaluation of a Role for Intracellular $Na^+$, $K^+$, $Ca^{2+}$, and $Mg^{2+}$ in Hyperthermic Cell Killing," *Radiation Res.* 105:187–200 (1986).

Warri et al., "Estrogen Suppression of erbB2 Expression is Associated with Increased Growth Rate of Zr–75–1 Human Breast Cancer Cells In Vitro and in Nude Mice," *Intl. J. Cancer* 49:616–623 (1991).

Wera et al., "Deregulation of Transitional Control of the 65 kDa Regulatory Subunit (PR65 Alpha) of Protein Phosphatase 2A leads to Multinucleated Cells," *J. Biol. Chem.* 270:21374–21381 (1995).

Wera et al., "Serine/Threonine Protein Phosphatasesm,". *J.* 311:17–29 (1995).

Wertz, et al., "Diverse Molecular Provocation of Programmed Cell Death," *TIBS* 21:359–364 (1996).

Zhen et al., "Cellular Analysis of the Mode of Action of Methyl–3–5–diiodo–4–(4'–Methoxyphenoxy) Benzoate (DIME) on Tumor Cells," *Intl. J. Oncol.* 10:905–910 (1997).

DIME 3 DAYS 10μM
X300

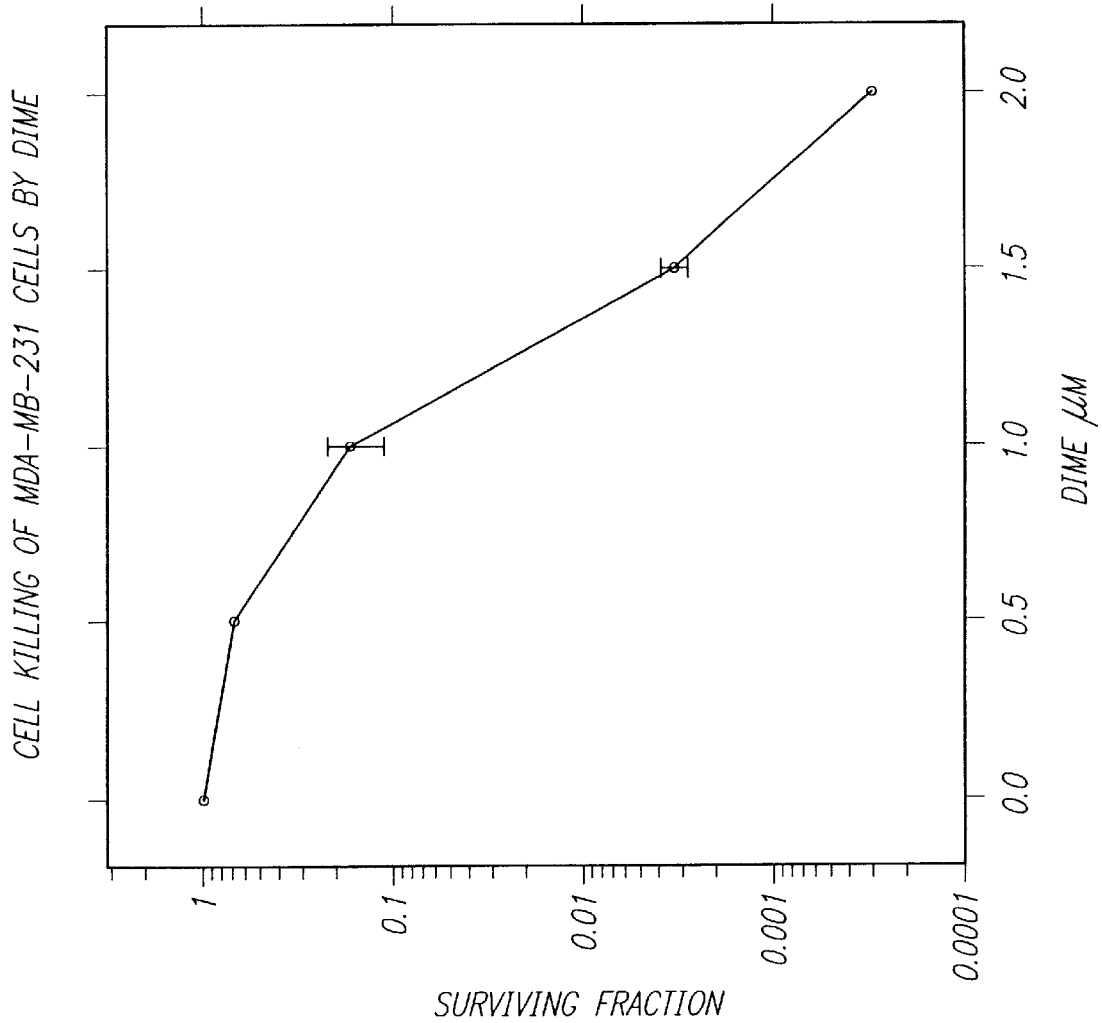

THE EFFECT OF DIME ON THE RESIDENCE TIME IN M PHASE OF MDA-MB 231 CELLS

METHOD OF TREATING MALIGNANT TUMORS WITH THYROXINE ANALOGUES HAVING NO SIGNIFICANT HORMONAL ACTIVITY

CROSS REFERENCE TO RELATED APPLICATIONS

This application is a continuation-in-part of U.S. Ser. No. 08/655,267, filed Jun. 4, 1996, now U.S. Pat. No. 5,736,576, the disclosure of which is incorporated hereby by reference.

FIELD OF THE INVENTION

The present invention relates generally to the field of cancer therapeutics. More specifically, the present invention relates to the use of thyroxine analogues having no significant hormonal activity, particularly methyl 3,5-diiodo-4-(4'-methoxyphenoxy)benzoate, as potent, selective and non-toxic anti-tumor agents.

BACKGROUND OF THE INVENTION

Malignant cancerous growths, due to their unique characteristics, pose serious challenges for modern medicine. These characteristics include uncontrollable cell proliferation resulting in unregulated growth of malignant tissue, an ability to invade local and even remote tissues, lack of differentiation, lack of detectable symptoms and most significantly, the lack of effective therapy and prevention.

Cancer can develop in any tissue of any organ at any age. The etiology of cancer is not clearly defined but mechanisms such as genetic susceptibility, chromosome breakage disorders, viruses, environmental factors and immunologic disorders have all been linked to a malignant cell growth and transformation.

Antineoplastic chemotherapy currently encompasses several groups of drugs including alkylating agents, purine antagonists and antitumor antibiotics. Alkylating agents alkylate cell proteins and nucleic acids preventing cell replication, disrupting cellular metabolism and eventually leading to cell death. Typical alkylating agents are nitrogen mustard, cyclophosphamide and chlorambucil. Toxicities associated with alkylating agents treatment include nausea, vomiting, alopecia, hemorrhagic cystitis, pulmonary fibrosis and an increased risk of developing acute leukemia.

Purine, pyrimidine and folate antagonists are cell cycle and phase specific and, in order to promote an anti-tumor effect, they require cells to be in the cell replication cycle and in the DNA synthesis phase of replication. The purine antagonists such as 6-mercaptopurine or 6-thioguanidine inhibit de novo purine synthesis and interconversion of purines. The pyrimidine antagonists, such as cytarabine, 5-fluorouracil or floxuridine inhibit DNA synthesis by inhibiting deoxycytidylate kinase and DNA polymerase.

Folate antagonists, e.g., methotrexates, bind tightly with the intracellular enzyme dihydrofolate reductase ultimately leading to cell death resulting from an inability to synthesize pyrimidines. Toxicities associated with the use of these compounds include alopecia, myelosuppression, vomiting, nausea, and cerebellar ataxia, among others.

Plant alkaloids such as vincristine, vinblastine or podophyllotoxins etoposide and teniposide generally inhibit mitosis and DNA synthesis and RNA dependent protein synthesis. Toxicities of these drugs are similar to those described above and include myopathy, myelosuppression, peripheral neuropathy, vomiting, nausea and alopecia.

Antitumor antibiotics such as doxorubicin, daunorubicin and actinomycin act as intercalators of DNA, preventing cell replication, inhibiting synthesis of DNA-dependent RNA and inhibiting DNA polymerase. Bleomycin causes scission of DNA and mitomycin acts as inhibitor of DNA synthesis by bifunctional alkylation. Toxicities of these antibiotics are numerous and severe and include necrosis, myelosuppression, anaphylactic reactions, anorexia, dose-dependent cardiotoxicity and pulmonary fibrosis.

Other compounds used for chemotherapeutical treatment of cancer are inorganic ions such as cisplatin, biologic response modifiers such as interferon, enzymes and hormones. All these compounds, similarly to those mentioned above, are accompanied by toxic adverse reactions.

Accordingly, it would be extremely advantageous to provide safe and non-toxic chemotherapeutic compositions which would effectively inhibit and/or suppress tumor cell proliferation and/or neoplastic growth. Furthermore, it would be extremely advantageous to provide safe, effective and non-toxic chemotherapeutic compositions that are easy to administer.

The identification of safe, effective, non-toxic, and orally administrable organic compounds capable of depressing or regressing malignant tumor growth in mammals and the use of such compounds to treat cancer is therefore desirable and the object of this invention.

SUMMARY OF THE INVENTION

The present invention relates to the use of thyroxine analogues having no significant hormonal activity, particularly methyl 3,5-diiodo-4-(4'-methoxy phenoxy)benzoate ("DIME") to depress or regress malignant tumor growth and to treat cancer. The method generally involves administering to a mammal an amount of a thyroxine analogue effective to depress or regress malignant tumor growth or to treat cancer. The thyroxine analogues typically are characterized as lacking significant hormonal activity.

In particular, the present invention relates to a method for treating a malignant tumor in a mammal, the method comprising administering to a mammal having a malignant tumor an amount of thyroxine analogue sufficient to depress growth of the malignant tumor, wherein the thyroxine analogue is characterized as being a comopund capable of causing about 35 percent or more inhibition of initial velocity of microtubule protein assembly in vitro, preferably about 45 percent or more, more preferably about 70 percent or more, and most preferably about 90 percent or mroe inhibition velocity of microtubule protein assembly in vitro.

In one illustrative embodiment, thyroxine analogues useful in the methods of the present invention are compounds having the structural formula:

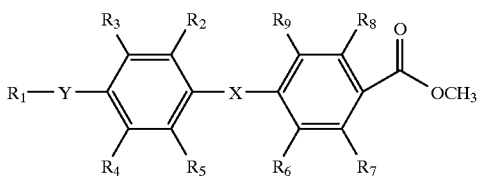

and pharmaceutically acceptable salts thereof, wherein:
X=O, S, $CH_2$, carboxy or absent;
Y=O or S;
$R_1$=methyl or ethyl;
$R_2$, $R_3$, $R_4$ and $R_5$ are each independently selected from the group consisting of: H, $(C_1-C_4)$ alkyl, $(C_1-C_4)$ alkenyl, $(C_1-C_4)$ alkynyl, hydroxy, $(C_1-C_4)$ alkoxy and halogen; and $R_6$, $R_7$, $R_8$ and $R_9$ are each independently selected from the group consisting of: H, ($C_1$–$C_4$) alkyl, ($C_1$–$C_4$) alkenyl, ($C_1$–$C_4$) alkynyl, hydroxy, ($C_1$–$C_4$) alkoxy, halogen, $NO_2$ and $NH_2$.

In another illustrative embodiment, thyroxine analogues useful in the methods of the present invention are compounds having the structural formula:

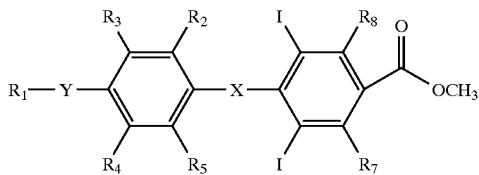

and pharmaceutically acceptable salts thereof, wherein:
X=O, S, $CH_2$, carboxy or absent;
Y=O or S;
$R_1$=methyl or ethyl;
$R_2$, $R_3$, $R_4$ and $R_5$ are each independently selected from the group consisting of: H, ($C_1$–$C_4$) alkyl, ($C_1$–$C_4$) alkenyl, ($C_1$–$C_4$) alkynyl, hydroxy, ($C_1$–$C_4$) alkoxy and halogen; and
$R_7$ and $R_8$ are each independently selected from the group consisting of: H, ($C_1$–$C_4$) alkyl, ($C_1$–$C_4$) alkenyl, ($C_1$–$C_4$) alkynyl, hydroxy, ($C_1$–$C_4$) alkoxy, halogen, $NO_2$ and $NH_2$.

In a preferred embodiment of the invention the thyroxine analogue is methyl 3,5-diiodo-4-(4'-methoxyphenoxy) benzoate ("DIME").

BRIEF DESCRIPTION OF THE FIGURES

FIG. 5. shows the effect of DIME concentration on the rates of colony formation by MDA-MB-231 cells.

FIGS. 16 (A, B and C) shows the hybridization of chromosomes 19 DNA in DIME-treated MDA-MB-231 cells (metaphase spread).

DETAILED DESCRIPTION OF THE INVENTION

Definitions

Figure 1:
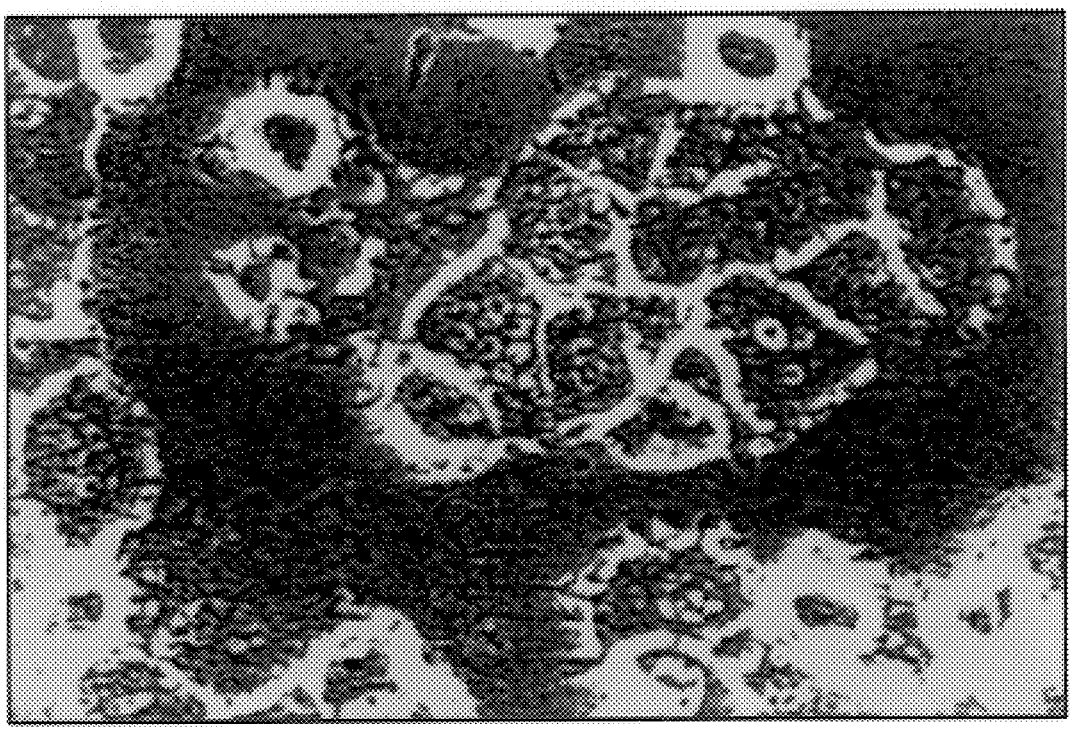
FIG. 1 is a photograph demonstrating the morphologic action of DIME on E-ras transformed bovine endothelial cells.

As used herein:

"Alkyl" refers to a saturated branched, straight chain or cyclic hydrocarbon radical. Typical alkyl groups include methyl, ethyl, propyl, isopropyl, cyclopropyl, butyl, isobutyl, cyclobutyl, tert-butyl, pentyl, hexyl and the like.

"Alkenyl" refers to an unsaturated branched, straight chain or cyclic hydrocarbon radical having at least one carbon-carbon double bond. The radical may be in either the cis or trans conformation about the double bond(s). Typical alkenyl groups include ethenyl, propenyl, isopropenyl, cyclopropenyl, butenyl, isobutenyl, cyclobutenyl, tert-butenyl, pentenyl, hexenyl and the like.

"Alkynyl" refers to an unsaturated branched, straight chain or cyclic hydrocarbon radical having at least one carbon-carbon triple bond. Typical alkynyl groups include ethynyl, propynyl, butynyl, isobutynyl, pentynyl, hexynyl and the like.

"Alkoxy" refers to an —OR radical, where R is alkyl, alkenyl or alkynyl, as defined above.

"Halogen" refers to fluoro, chloro, bromo and iodo substituents.

"Mammal" refers to animals or humans.

"Pharmaceutically acceptable salt" refers to those salts of compounds which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salts include, for example, alkali metal salts such as sodium and potassium, alkaline earth salts and ammonium salts.

"Pharmacophore" refers to the critical three-dimensional arrangement of molecular moieties or fragments (or the distribution of electron density) that is recognized by a receptor (*Burger's Medicinal Chemistry and Drug Delivry Vol. I: Principles and Practice* 619, 5th Edition, John Wiley & Sons, New York).

"Therapeutically effective amount" refers to an amount of a compound or composition effective to depress, suppress or regress malignant cell growth or result in amelioration of symptoms associated with cancerous diseases.

Description of Specific Embodiments

The present invention relates to methods of treating malignant tumors and cancer in mammals with analogues of thyroxine which are characterized as having no significant hormonal activity. Preferably, the present invention is based, in part, on the surprising discovery that certain analogues of thyroxine that do not exhibit hormonal activity are potent, selective and non-toxic inhibitors of malignant tumor growth. The preferred thyroxine analogue is referred to herein as DIME. Thyroxine, an amino acid of the thyroid gland (*Merck Index,* 1989, 9348:1483) and thyroxine analogues are well-known in the art. It is well established in the literature that thyroid hormones, specifically thyroxines T3 and T4, have two distinct types of biological actions: one on cell metabolism, the second on cell differentiation and development (Jorgensen, 1978, "Thyroid Hormones and Analogues II. Structure-Activity Relationships," In: *Hormonal Proteins and Peptides, Vol. VI, pp.* 107–204, C.H. Li, ed., Academic Press, NY). For example, thyroxine suppresses uptake of iodine by the thyroid (Money et al., 1959, "The Effect of Various Thyroxine Analogues on Suppression of Iodine-131 Uptake by the Rat Thyroid," *Endocrinology* 64:123–125) and induces cell differentiation as studied by tadpole metamorphosis (Money et al., 1958, "The Effect of Change in Chemical Structure of Some Thyroxine Analogues on the Metamorphosis of Rana Pipiens Tadpoles," *Endocrinology* 63:20–28). Additionally, thyroxine and certain thyroxine analogues depress growth of non-malignant mouse pituitary thyrotropic tumors (Kumaoka et al., 1960, "The Effect of Thyroxine Analogues on a Transplantable Mouse Pituitary Tumor," *Endocrinology* 66:32–38; Grinberg et al., 1962, "Studies with Mouse Pituitary Thyrotropic Tumors. V. Effect of Various Thyroxine Analogs on Growth and Secretion," *Cancer Research* 22:835–841). The structural requirements of thyroxine and thyroxine analogues for metabolic stimulation and induction of cell differentiation are not identical (see Jorgensen, 1978, "Thyroid Hormones and Analogues II. Structure-Activity Relationships," In: *Hormonal Proteins and Peptides,* Vol. VI, p. 150, C.H. Li, ed., Academic Press, NY). For example, Money et al. have found that there is no correlation between suppression of thyroid iodine uptake and induction of tadpole metamorphosis (Money et al., 1958, "The Effect of Change in Chemical Structure of Some Thyroxine Analogues on the Metamorphosis of Rana Pipiens Tadpoles," *Endocrinology* 63:20–28). Based on these observations, it was conceived that as yet unidentified cellular responses may be altered or induced by certain thyroxine analogues which do not exhibit either mode of action (metabolic or differentiating) exhibited by thyroxine T3 and T4.

The Compounds

Thyroxine analogues useful in the methods of the present invention are generally compounds having the structural formula:

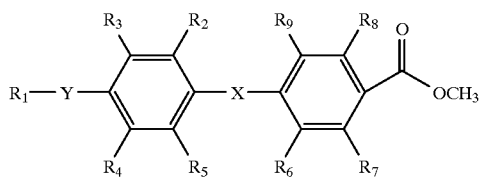

and pharmaceutically acceptable salts thereof, wherein:
X=O, S, $CH_2$, carboxy or absent;
Y=O or S;
$R_1$=methyl or ethyl;
$R_2$, $R_3$, $R_4$ and $R_5$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy and halogen; and
$R_6$, $R_7$, $R_8$ and $R_9$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$ and $NH_2$.

In a preferred embodiment, thyroxine analogues useful in the methods of the present invention are compounds having the structural formula:

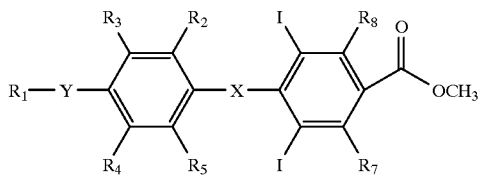

and pharmaceutic ally acceptable salts thereof, wherein:
X=O, S, $CH_2$, carboxy or absent;
Y=O or S;
$R_1$=methyl or ethyl;
$R_2$, $R_3$, $R_4$ and $R_5$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy and halogen; and
$R_7$ and $R_8$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$ and $NH_2$.
In a particularly preferred embodiment, the thyroxine analogue is methyl 3,5-diiodo-4-(4'-methoxyphenoxy)benzoate ("DIME"). Thyroxine analogues such as DIME have been described in the literature. However, unlike thyroxine, DIME was reported to have no significant metabolic or cell differentiating activity (as determined by tadpole metamorphosis) (Money et al., 1958, "The Effect of Change in Chemical Structure of Some Thyroxine Analogues on the Metamorphosis of Rana Pipiens Tadpoles," *Endocrinology* 63:20–28; Stasilli et al., 1959, "Antigoitrogenic and Calorigenic Activities of Thyroxine Analogues in Rats," *Endocrinology* 64:62–82). For example, uptake of iodine into the thyroid of rats is only marginally (15%) inhibited by DIME as compared to thyroxine (Money et al., 1959, "The Effect of Various Thyroxine Analogues on Suppression of Iodine-131 Uptake by the Rat Thyroid," *Endocrinology* 64:123–125). Furthermore, DIME was reported to have no inhibitory activity against the growth of a non-malignant mouse pituitary adenoma (Kumaoka et al., 1960, "The Effect of Thyroxine Analogues on a Transplantable Mouse Pituitary Tumor," *Endocrinology* 66:32–38; Grinberg et al., 1962, "Studies with Mouse Pituitary Thyrotropic Tumors. V. Effect of Various Thyroxine Analogs on Growth and Secretion," *Cancer Research* 22:835–841). No studies with malignant cells have been reported. It has now been discovered that certain thyroxine analogues having no significant hormonal activity, particularly DIME, not only inhibit the growth of a variety of malignant cell types (see Table 3), but induce tumor cell apoptosis preceded by micronucleation as well. These cytostatic and cytocidal activities are sensitive to structure. Testing of thirteen structural analogues and homologues of DIME indicates that even minor alterations of the methyl ester and 4'-methoxy substituents renders the molecule completely inactive. Whereas DIME is highly active both in cellular assays and in vivo, the 4'-propoxy and ethyl ester homologues are completely inactive. Accordingly, DIME defines a critical arrangement of molecular moieties, or a pharmacophore, having specific cytostatic and cytocidal activity, and consequently significant chemotherapeutic potential. While not intending to be bound by theory, it is believed that the most probable molecular mode of action of the thyroxine analogues described herein is cell cycle inhibition and induction of apoptosis. Progression of eukaryotic cells through the cell division cycle is primarily controlled by the activity of cyclin-dependent protein kinases. The best studied event is the transition from G2 to M phase, which is controlled by cdc2 kinase complexed with cyclin B (for a review see, Dunphy, 1994, *Trends Cell. Biol.* 4:202–207). cdc2 kinase activation requires phosphorylation, a process that is regulated by protein phosphatase 2A (for a review, see, Wera & Hennings, 1995, *Biochem. J.* 311:17–29). It has been discovered that the thyroxine analogues described herein exert specific activation of protein phosphatase 2A both in vitro and in vivo. In vivo, activation of protein phosphatase 2A coincides with inhibition of cdc2 kinase and dephosphorylation of MAP kinase and topoisomerase II, rendering both of the latter enzymes inactive. DIME has no metabolic action, nor does it inhibit the biosynthetic pathways of DNA, RNA or proteins. Thus, the most probable mode of action is cell cycle inhibition and induction of apoptosis via dephosphorylation of these critical regulatory proteins. Accordingly, activation of phosphatase 2A and concomitant inhibition of cdc2 kinase is an important and powerful therapeutic target for the treatment of cancer. While alterations at the ester and 4'-positions appear to significantly affect the effectivity of DIME, thyroxine analogues useful for depressing malignant tumor growth and treating cancer are not limited to DIME. For example, the 4'-ethoxy homologue exhibits about 25–30% maximal cytocidal action on human cancer cells as compared to DIME (Example 4). It is also expected that DIME may be substituted at the aromatic ring positions or bridge oxygen without significant loss of activity. It is known that the aromatic rings of thyroxine are not contained within the same plane (Jorgensen, 1978, "Thyroid Hormones and Analogues II. Structure-Activity Relationships," In: *Hormonal Proteins and Pegtides,* Vol. VI, pp. 107–204, C.H. Li, ed., Academic Press, NY). It is also known that the ring positions of both of the aromatic rings in thyroxine can be substituted with a variety of substituents, including alkyl, halogen, nitro and amino groups with varying degrees of retention of hormonal activity (ibid). Furthermore, the ether oxygen connecting the rings can be absent or replaced with a variety of groups or atoms that do not confine the aromatic rings to the same plane, such as, for example, a methylene group, a carboxy group or sulfur, without significant loss of hormonal activity (ibid). Accordingly, it is expected and predictable that similar substitutions on DIME will not effect significant loss of anti-cancer activity. Significantly, the 2'-chloro analogue of DIME exhibited about 25% maximal inhibitory action on the growth of human cancer cells as compared to DIME (Example 5). Due to the stringent correlation between in vitro and in vivo efficacy (see, Examples 2–7), effective compounds useful in the methods of the invention may be conveniently identified in in vitro assay screening tests. Such tests may screen for the ability of a particular compound to activate protein phosphatase 2A, as described in Examples 2–3. Typically, compounds useful in the methods of the present invention will increase protein phosphatase 2A activity by a factor of about two to three, as measured by the assay described in Example 2 or 3. Such tests may also screen for the ability of a particular compound to inhibit malignant tumor cell growth in vitro or in vivo or abolish tumorigenicity of malignant cells, as described in Examples 4–6. Generally, active compounds useful in the methods of the present invention will exhibit an $I_{50}$ (concentration of compound lethal to 50% of a cell culture as compared to a control culture) in the range of about 0.5 $\mu$m to 5.0 $\mu$m, as measured by the assay described in Example 4. As will be appreciated by the skilled artisan, many varieties of malignant tumor cell cultures and cell lines may be used to screen for activity, including but not limited to HL-60, HT-144, E-ras-20, DU-145, MDA-168, MCF-7, 855-2 and MDA-MB-231. Of course, other in vitro and/or in vivo assays as will be apparent to the skilled artisan to screen for anti-tumor and/or anti-cancer activity may also be employed to identify effective thyroxine analogues useful in the present invention. The chemical formulae referred to herein may exhibit the phenomena of tautomerism or conformational isomerism. As the formulae drawings within this specification can only represent one of the possible tautomeric or conformational isomeric forms, it should be understood that the invention encompasses any tautomeric or conformational isomeric forms which exhibit biological or pharmacological activities similar to DIME, as described herein. In addition to the above-described compounds and their pharmaceutically acceptable salts, the invention may employ, where applicable, solvated as well as unsolvated forms of the compounds (e.g. hydrated forms). The compounds described herein may be prepared by any process known to be applicable to the preparation of chemical compounds. Suitable processes are illustrated by the representative examples. Necessary starting materials may be obtained by standard procedures of organic chemistry.

Cancers

The thyroxine analogues described herein are useful for treating a wide variety of cancers. Such cancers include, by way of example and not limitation, carcinomas such as pharynx, colon, rectal, pancreatic, stomach, liver, lung, breast, skin, prostate, ovary, cervical, uterine and bladder cancers; leukemias; lymphomas; gliomas; retinoblastomas; and sarcomas. In a preferred embodiment of the invention, the cancer is associated with the formation of solid tumors including, by way of example and not limitation, mammary and prostatic cancers.

Pharmaceutical Formulations And Routes Of Administration

A thyroxine analogue useful in the present invention can be administered to a human patient per se, in the form of a pharmaceutically acceptable salt, or in the form of a pharmaceutical composition where the compound is mixed with suitable carriers or excipient(s) in a therapeutically effective amount, i.e., at doses effective to depress or suppress malignant cell growth or result in amelioration of symptoms associated with cancerous diseases.

Routes Of Administration

The thyroxine analogues and pharmaceutical compositions described herein may be administered by a variety of routes. Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Alternatively, one may administer the compound in a local rather than systemic manner, for example via injection of the compound directly into a solid tumor, often in a depot or sustained release formulation. Furthermore, one may administer the compound in a targeted drug delivery system, for example, in a liposome coated with tumor-specific antibody. The liposomes will be targeted to and taken up selectively by the tumor. In a preferred embodiment, the thyroxine analogues and pharmaceutical compositions described herein are administered orally.

Composition/Formulation

The pharmaceutical compositions described herein may be manufactured in a manner that is itself known, e.g., by means of conventional mixing, dissolving, granulating, dragee-making, levigating, emulsifying, encapsulating, entrapping or lyophilizing processes. Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art. For oral administration, the compounds can be formulated readily by combining with pharmaceutically acceptable carriers that are well known in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. A suitable pharmaceutical carrier for hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% (w/v) benzyl alcohol, 8% (w/v) of the nonpolar surfactant polysorbate 80, and 65% (w/v) polyethylene glycol 300, made up to volume in absolute ethanol. The VPD co-solvent system (VPD:5W) consists of VPD diluted 1:1 with a 5% (w/v) dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Other formulations suitable for administering the thyroxine analogues described herein will be apparent to those having skill in the art, and may be found, for example, in *Remington's Pharmaceutical Sciences,* Mack Publishing Co., Easton, Pa., latest edition.

Effective Dosages

Pharmaceutical compositions suitable for use in the present invention include compositions wherein the active ingredients are contained in a therapeutically effective amount. Determination of an effective amount is well within the capability of those skilled in the art, especially in light of the detailed disclosure provided herein. For any compound used in the method of the invention, a therapeutically effective dose can be estimated initially from cell culture assays. For example, a dose can be formulated in animal models to achieve a circulating concentration range that includes the $I_{50}$ as determined in cell culture (i.e., the concentration of test compound that is lethal to 50% of a cell culture) or the $I_{100}$ as determined in cell culture (i.e., the concentration of compound that is lethal to 100% of a cell culture). Such information can be used to more accurately determine useful doses in humans. Initial dosages can also be formulated by comparing the effectiveness of the thyroxine analogues described herein in cell culture assays with the effectiveness of known anti-cancer drugs such as vincristine. In this method an initial dosage can be obtained by multiplying the ratio of effective concentrations obtained in cell culture assay for the thyroxine analogue and a known anti-cancer drug by the effective dosage of the known anti-cancer drug. For example, if a thyroxine analogue is twice as effective in cell culture assay than vincristine (i.e., the $I_{50}^{DIME}$ is equal to one half times the $I_{50}^{vincristine}$ in the same assay), an initial effective dosage of the thyroxine analogue would be one-half the known dosage for vincristine. Using these initial guidelines one having ordinary skill in the art could determine an effective dosage in humans. Initial dosages can also be estimated from in vivo data. For example, it has been found that 250 mg/kg administered by gavage once daily, 5 days a week for 32 days significantly depressed the growth of mammary cancer xenografts (MDA-MB-231) in nude mice (see Example 7.3). Studies have also shown that DIME has a half-life (to) in serum of about 2–2.5 hours, and is 87% bioavailable by per os administration (see Example 7.2). One having ordinary skill in the art could readily optimize administration to humans based on this data. Dosage amount and interval may be adjusted individually to provide plasma levels of the active compound which are sufficient to maintain therapeutic effect. Usual patient dosages for oral administration range from about 50–2000 mg/kg/day, commonly from about 250–1000 mg/kg/day, preferably from about 500–700 mg/kg/day and most preferably from about 350–550 mg/kg/day. Preferably, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation. The amount of composition administered will, of course, be dependent on the subject being treated, on the subject's weight, the severity of the affliction, the manner of administration and the judgment of the prescribing physician. The chemotherapy may be repeated intermittently while tumors are detectable or even when they are not detectable. Moreover, due to its apparent nontoxicity (discussed below), the therapy may be provided alone or in combination with other anti-cancer or other drugs, such as for example AZT, anti-inflammatories, antibiotics, corticosteroids, vitamins and the like. Possible synergism between the thyroxine analogues described herein and other drugs is expected and predictable. In addition, possible synergism between a plurality of thyroxine analogues is also expected and predictable.

Toxicity

Toxicity and therapeutic efficacy of the thyroxine analogues described herein can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$.

Compounds which exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch.1, p.1). One of the advantages, among others, of using the thyroxine analogues described herein to treat cancer is their lack of toxicity. For example, it has been found that a daily oral dose of 1 g/kg administered for 12–15 days produced no ill effects in nude mice (see Example 7.1). Since the i.v. serum half-life ($t_{1/2}$) of DIME is about 2–2.5 hours, repeated daily dosages of the thyroxine analogues described herein without ill effects is predictable.

The invention having been described, the following examples are offered to illustrate the subject invention by way of example, not by way of limitation.

EXAMPLE 1

Compound Syntheses

Fourteen thyroxine analogues were synthesized, purified and characterized. A summary of the structure of each synthesized compound and select physical data is provided at Table 1, below.

Part I. The Preparation of Tyrosine and Some of its Derivatives, and a New Route to Thyroxine," *J. Chem. Soc.* 1949 (Supp. Issue No. 1):S185–S190, and recrystallized from 95% ethanol. Melting point: 153°–155° C.

Mass spectrum: FAB, m/z (relative intensity): 510 ($M^+$, 100), 479 (4.5), 384 (4.5). High-resolution data for the M+ peak: calculated for $C_{15}H_{12}I_2O_4$, 509.882513; found, 509.882960 (deviation=−0.9 ppm).

$^1H$ NMR spectrum in DMSO-$d_6$ (δ (ppm) values relative to TMS): 3.719 (3H, singlet), 3.876 (3H, singlet), 6.693 (2H, doublet, J=9.45 Hz, plus fine-splitting), 6.845 (2H, doublet, H=9.36 Hz, plus fine-splitting), 8.390 (2H, singlet).

1.2 Methyl 3,5-diiodo-4-(4'-ethoxyphenoxy)benzoate (Compound 2)

Methyl 3,5-diiodo-4-(4'-ethoxyphenoxy)benzoate (Compound 2) was synthesized using the general methodology of Borrows, et al., 1949, "The Synthesis of Thyroxine and Related Substances. Part I. The Preparation of Tyrosine and Some of its Derivatives, and a New Route to Thyroxine," *J. Chem. Soc.* 1949 (Supp. Issue No. 1):S185–S190.

1.2.1 Methyl 3,5-dinitro-4-(4'-ethoxyphenoxy)benzoate

In a 50-ml flask at ambient temperature 4-ethoxy-phenol (Aldrich) (1492 mg, 10.8 mmoles) was stirred with 2.0 M aqueous KOH (5.50 ml) to form potassium 4-ethoxyphenolate. Methyl 4-chloro-3,5-dinitrobenzoate (Ullmann, 1909, *Annalen der Chemie* 366:92–93; commercial source: Spectrum Chemical Company, Gardena, Calif.; 2606 mg, 10.0 mmoles) was added, the mixture heated to reflux for 1 hour and chilled in an ice-bath, whereupon a rubbery mass of product deposited. Cold aqueous 1.0 M KOH (20 ml) was added, and upon continued chilling the

TABLE 1

Thyroxine Analogues Synthesized

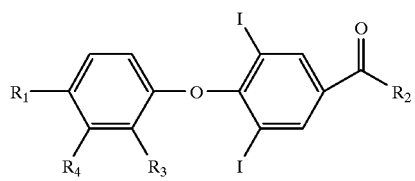

| No. | $R_1$ | $R_2$ | $R_3$ | $R_4$ | m.p. (° C.) | Formula | Mass (calcd.) | Mass (found) |
|---|---|---|---|---|---|---|---|---|
| 1 | $CH_3O$ | $CH_3O$ | H | H | 153–155 | $C_{15}H_{12}I_2O_4$ | 509.882513 | 509.882960 |
| 2 | EtO | $CH_3O$ | H | H | 123–125 | $C_{16}H_{14}I_2O_4$ | 523.898163 | 523.898737 |
| 3 | n-PrO | $CH_3O$ | H | H | 114–116 | $C_{17}H_{16}I_2O_4$ | 537.913813 | 537.914014 |
| 4 | n-BuO | $CH_3O$ | H | H | 82–84 | $C_{18}H_{18}I_2O_4$ | 551.929463 | 551.930000 |
| 5 | $CH_3O$ | EtO | H | H | 96–98 | $C_{16}H_{14}I_2O_4$ | 523.898163 | 523.898202 |
| 6 | $CH_3O$ | HO | H | H | 233–235 | $C_{14}H_{10}I_2O_4$ | ref[a] | |
| 7 | $CH_3O$ | $H_2N$ | H | H | 207–209 | $C_{14}H_{11}I_2NO_3$ | 494.882847 | 494.881880 |
| 8 | $CH_3O$ | $(CH_3)HN$ | H | H | 181–183 | $C_{15}H_{13}I_2NO_3$ | 508.898497 | 508.898971 |
| 9 | $CH_3O$ | $(CH_3)_2N$ | H | H | 162–164 | $C_{16}H_{15}I_2NO_3$ | 522.914148 | 522.914364 |
| 10 | HO | $CH_3O$ | H | H | 204 (dec.)[b] | $C_{14}H_{10}I_2O_4$ | 495.866863 | 495.867453 |
| 11 | H | $CH_3O$ | H | H | 142–144 | $C_{14}H_{10}I_2O_3$ | 479.871948 | 479.872553 |
| 12 | I | $CH_3O$ | H | H | 139–141 | $C_{14}H_9I_3O_3$ | 605.768600 | 605.767839 |
| 13 | H | $CH_3O$ | H | $CH_3O$ | 123–125 | $C_{15}H_{12}I_2O_4$ | 509.882513 | 509.882387 |
| 14 | $CH_3O$ | $CH_3O$ | Cl | H | 132–134 | $C_{15}H_{11}ClI_2O_4$ | 543.843541 | 543.843424 | ref[a]: Compound 6 was prepared according to Borrows et al., J. Chem. Soc. 1949:S185–S190.
[b]: Decomposition tempreature.

1.1 Methyl 3 5-diiodo-4-(4'-methoxyphenoxy)benzoate (Compound 1)

Methyl 3,5-diiodo-4-(4'-methoxyphenoxy)benzoate (Compound 1) was prepared as described in Borrows et al., 1949, "The Synthesis of Thyroxine and Related Substances.

product solidified. The yellow-orange solid was broken-up, collected on a suction filter, rinsed with water and dried. The material (3.08 g) was crystallized from hot 95% ethanol (50 ml) to give 2.56 g (70.6 % yield) of methyl 3,5-dinitro-4-(4'-ethoxyphenoxy)benzoate. Melting point: 101°–103° C.

Mass spectrum (EI): M+ in high-resolution: calculated for $C_{16}H_{14}N_2O_8$: 362.075016; found, 362.074793 (deviation= 0.6 ppm).

1.2.2 Methyl 3,5-diiodo-4(4'-ethoxyphenoxy)benzoate

A portion (724.4 mg, 2.00 mmoles) of methyl 3,5-dinitro-4-(4'-ethoxyphenoxy)benzoate was dissolved in glacial acetic acid (50 ml), mixed with 10% palladium-on-carbon catalyst (Aldrich) (200 mg) in a Parr Model 4561 Mini-Reactor, charged with an atmosphere of $H_2$ (43 psi) and rapidly stirred at ambient temperature until the pressure-drop due to the reaction ceased (6 minutes, 16 psi final). The mixture was immediately filtered through a bed of celite to remove the catalyst and stripped of acetic acid solvent on a rotary evaporator to yield a brown, oily residue representing the crude 3,5-diamine derivative. The crude diamine was dissolved in glacial acetic acid (6.0 ml) and tetrazotized by adding it dropwise over a period of 3 minutes to a stirred, ice-cold solution of sodium nitrite (345 mg, 5 mmoles) in concentrated sulfuric acid (3.5 ml). After stirring for 30 minutes at ice-bath temperature, the viscous mixture was pipetted into a rapidly stirred solution of potassium iodide (3.0 g) in distilled water (2.5 ml) at ambient temperature. The dark mixture was stirred for 30 minutes and finally heated to 70° C. for 5 minutes. The mixture was poured into ethyl acetate (100 ml) and water (50 ml) was added. The two-phase mixture was transferred to a separatory funnel, additional ethyl acetate (50 ml) and water (50 ml) added, and the product extracted into the ethyl acetate. The organic (ethyl acetate) layer was washed with two additional portions of water (50 ml each) and dried over anhydrous sodium sulfate. Subsequent removal of ethyl acetate by evaporation yielded a dark, tarry residue.

This crude product was dissolved in acetone (8 ml) and purified by preparative thin-layer chromatography plates (five) (Whatman, silica-gel, 1000 μm layer, 20 cm×20 cm, with fluorescent indicator). The plates were developed in n-hexane:ethyl acetate:acetic acid (3:1:0.8 v/v/v). The product band ($R_f$=0.84), visualized under UV light, was collected from the respective plates, pooled, and eluted from the silica-gel (held in a sintered glass funnel) with ethyl acetate (3×50 ml). Removal of ethyl acetate yielded an off-white solid which was crystallized from 95% ethanol (10 ml). Yield: 275 mg total of two crops of white crystals (26% based on 2 mmoles of the dinitro precursor). Melting point: 123°–125° C.

Mass spectrum: EI, m/z (relative intensity): 524 (M+, 100), 496 (16.7), 310 (9.1), 242 (6.1), 211 (7.6), 155 (6.1). High-resolution data for the M+ peak: calculated for $C_{16}H_{14}I_2O_4$: 523.898163; found, 523.898737 (deviation=-1.1 ppm).

$^1$H NMR spectrum in DMSO-$d_6$ (δ (ppm) values relative to TMS): 1.303 (3H, triplet, J=6.94 Hz), 3.877 (3H, singlet), 3.971 (2H, quartet, J=6.95 Hz), 6.678 (2H, doublet, J=8.98 Hz, plus fine-splitting), 6.879 (2H, doublet, J=9.06 Hz, plus fine-splitting), 8.389 (2H, singlet).

1.3 Methyl 3,5-diiodo-4-(4'-n-propoxyphenoxy)benzoate (Compound 3)

Methyl 3,5-diiodo-4-(4'-n-propoxyphenoxy)benzoate (Compound 3) was prepared as described in Example 1.2. The dinitro precursor was synthesized by treating an aqueous solution of potassium 4-n-propoxy-phenolate (prepared from commercial 4-n-propoxy-phenol) with methyl 4-chloro-3,5-dinitrobenzoate. The dinitro product was reduced by $H_2$/Pd(C) to the diamine derivative, which was then tetrazotized with $NaNO_2$/$H_2SO_4$ and converted to the diiodo product by reaction with potassium iodide (Sandmeyer reaction). Purification was by preparative TLC and crystallization.

1.4 Methyl 3,5-diiodo-4-(4'-n-butoxyphenoxy)benzoate (Compound 4)

Methyl 3,5-diiodo-4-(4'-n-butoxyphenoxy)benzoate (Compound 4) was prepared as described in Example 1.2. The dinitro precursor was synthesized by treating an aqueous solution of potassium 4-n-butoxyphenolate (prepared from commercial 4-n-butoxyphenol) with methyl 4-chloro-3,5-dinitrobenzoate. The dinitro product was reduced by $H_2$/Pd(C) to the diamine derivative, which was then tetrazotized with $NaNO_2$/$H_2SO_4$ and converted to the diiodo product by reaction with potassium iodide (Sandmeyer reaction). Purification was by preparative TLC and crystallization.

1.5 Ethyl 3,5-diiodo-4-(4'-methoxyphenoxy)benzoate (Compound 5)

Ethyl 3,5-diiodo-4-(4'-methoxyphenoxy)benzoate (Compound 5) was synthesized by way of 3,5-diiodo-4-(4'-methoxyphenoxy)benzoyl chloride, the latter having been described in Borrows et al., 1949, *J. Chem. Soc.* 1949: S185–S190. Thus, in a 10 ml flask 3,5-diiodo-4-(4'-methoxyphenoxy)benzoic acid (99.2 mg, 0.200 mmole) was converted to 3,5-diiodo-4-(4'-methoxyphenoxy)benzoyl chloride. After removal of excess thionyl chloride under vacuum, anhydrous ethanol (5.0 ml) was added with stirring and the mixture heated to 70° C. for 5 minutes. Excess ethanol was removed and the dry residue dissolved in hot 95% ethanol (4.0 ml), from which the product ester crystallized in the refrigerator (3° C.). Yield: 55.8 mg (53%) of buff-colored crystals. Melting point: 96°–98° C.

Mass spectrum (EI): High-resolution data for the M+ peak: calculated for $C_{16}H_{14}I_2O_4$, 523.898163; found, 523.898202 (deviation=-0.1 ppm).

$^1$H NMR spectrum in DMSO-$d_6$ (δ (ppm) values relative to TMS): 1.336 (3H, triplet, J=7.19 Hz), 3.717 (3H, singlet), 4.336 (2H, quartet, J=7.06 Hz), 6.695 (2H, doublet, J=9.34 Hz, plus fine-splitting), 6.895 (2H, doublet, J=9.20, plus fine-splitting), 8.389 (2H, singlet).

1.6 3.5-diiodo-4-(4'-methoxyphenoxy)benzoic acid (Compound 6)

3,5-diiodo-4-(4'-methoxyphenoxy)benzoic acid (Compound 6) was synthesized as described in Borrows et al., 1949, *J. Chem. Soc.* 1949: S185—S190.

1.7 3,5-diiodo-4-(4'-methoxyphenoxy)benzamide (Compound 7)

3,5-diiodo-4-(4'-methoxyphenoxy)benzamide (Compound 7) was synthesized by amidating Compound 1. In a 125 ml flask, methyl 3,5-diiodo-4-(4'-methoxyphenoxy)benzoate (Compound 1) (100 mg, 0.196 mmole) was dissolved in anhydrous methanol (60 ml). Anhydrous ammonia gas was bubbled into the solution for 5 minutes at a moderate rate at ambient temperature. After standing for 1 hour in the stoppered flask, the ammonia gas treatment was repeated (5 minutes) and the mixture allow to stand in the stoppered flask for 48 hours. The methanol/ammonia was removed by rotary evaporation, the dry residue dissolved in methanol:water (7:3 v/v) (30 ml) and crystallized in the refrigerator (3° C.). Yield: 58.3 mg (60% yield) of buff-colored crystals. Melting point: 207°–209° C.

Mass spectrum (FAB): High-resolution data for the M+ peak: calculated for $C_{14}H_{11}I_2No_3$, 494.882847; found, 494.881880 (deviation=2.0 ppm).

$^1$H NMR spectrum in DMSO-$d_6$ (δ (ppm) values relative to TMS): 3.716 (3H, singlet), 6.682 (2H, doublet, J=8.93 Hz), 6.895 (2H, doublet, J=8.99 Hz), 7.528 (1H, singlet), 8.113 (1H, singlet), 8.402 (2H, singlet).

1.8 3.5-diiodo-4-(4'-methoxyphenoxy)-N-methyl benzamide (Compound 8)

3,5-diiodo-4-(4'-methoxyphenoxy)-N-methyl benzamide (Compound 8) was prepared by way of 3,5-diiodo-4-(4'-methoxyphenoxy)benzoyl chloride (see, Example 1.5). The acid chloride was reacted with excess methylamine in tetrahydrofuran at ambient temperature (1 hour), filtered to remove methylamine-hydrochloride precipitate, the solvent evaporated and the product crystallized from 95% ethanol.

1.9 3.5-diiodo-4-(4'-methoxyphenoxy)-N,N-dimethyl benzamide (Compound 9)

3,5-diiodo-4-(4'-methoxyphenoxy)-N,N-dimethyl benzamide (Compound 9) was prepared way of 3,5-diiodo-4-(4'-methoxyphenoxy)benzoyl chloride (see, Example 1.5). The acid chloride was reacted with excess methylamine in tetrahydrofuran at ambient temperature (1 hour), filtered to remove methylamine-hydrochloride precipitate, the solvent evaporated and the product crystallized from absolute ethanol.

1.10 Methyl 3,5-diiodo-4-(4'-hydroxvphenoxy) benzoate (Compound 10)

Methyl 3,5-diiodo-4-(4'-hydroxyphenoxy) benzoate (Compound 10) was prepared as described in Example 1.2. The dinitro precursor was prepared by reacting 4-chloro-3,5-dinitrobenzoate with hydroquinone in pyridine solution as described in Borrows et al., 1949, "The Synthesis of Thyroxine Related Substances. Part II. The Preparation of Dinitrodiphenyl Ethers," *J. Chem. Soc.* 1949 (Supp. Issue No. 1):S190–S199.

1.11 Methyl 3 5-diiodo-4-phenoxybenzoate (Compound 11)

Methyl 3,5-diiodo-4-phenoxybenzoate (Compound 11) was prepared as described in Example 1.2. The dinitro precursor was synthesized by treating an aqueous solution of potassium phenolate (prepared from commercial phenol) with methyl 4-chloro-3,5-dinitrobenzoate. The dinitro product was reduced by $H_2$/Pd(C) to the diamine derivative, which was then tetrazotized with $NaNO_2$/$H_2SO_4$ and converted to the diiodo product by reaction with potassium iodide (Sandmeyer reaction). Purification was by preparative TLC and crystallization.

1.12 Methyl 3,5-diiodo-4-(4'-iodophenoxy)benzoate (Compound 12)

Methyl 3,5-diiodo-4-(4'-iodophenoxy)benzoate (Compound 12) was synthesized as described in Example 1.2. Since the iodo-substituent in the dinitro precursor is itself labile with respect to reduction by $H_2$/Pd(C), the iodo-dinitro precursor was reduced to the iodo-diamine with iron powder in acetic acid/95% ethanol (see, e.g., Gemmill et al., 1956, "3-Iodo-, 3,3'-Diiodo- and 3,3'-Diiodo-5-bromothyroxine," *J. Am. Chem. Soc.* 78:2434–2436). The iodo-diamine was then tetrazotized and converted to the triiodo product using the Sandmeyer reaction. After purification by preparative TLC, the product (m.p. 139°–141° C.) was crystallized from ethanol.

Mass spectrum (EI): High resolution data for the M+ peak: calculated for $C_{14}H_9O_3I_3$, 605.768600; found, 605.767839 (deviation=1.3 ppm).

$^1$H NMR spectrum in DMSO-$d_6$ (δ (ppm) values relative to TMS): 3.879 (3H, singlet), 6.628 (2H, doublet, J=8.97 Hz plus fine-splitting), 7.670 (2H, doublet, J=9.12 Hz plus fine-splitting), 8.396 (2H, singlet).

1.13 Methyl 3,5-diiodo-4-(3'-methoxyphenoxy) benzoate (Compound 13)

Methyl 3,5-diiodo-4-(3'-methoxyphenoxy)benzoate (Compound 13) was synthesized as described in Example 1.2. The dinitro precursor was synthesized by treating an aqueous solution of potassium 3-methoxy phenolate (prepared from commercial 3-methoxyphenol) with methyl 4-chloro-3,5-dinitrobenzoate. The dinitro product was reduced by $H_2$/Pd(C) to the diamine derivative, which was then tetrazotized with $NaNO_2$/$H_2SO_4$ and converted to the diiodo product by reaction with potassium iodide (Sandmeyer reaction). Purification was by preparative TLC and crystallization.

1.14 Methyl 3,5-diiodo-4-(2'-chloro-4'-methoxyphenoxy) benzoate (Compound 14)

Methyl 3,5-diiodo-4-(2'-chloro-4'-methoxyphenoxy) benzoate (Compound 14) was synthesized by the general methodology described in Example 1.2, but with an alternate method for the reduction of the dinitro precursor.

1.14.1 Methyl 3,5-dinitro-4-(2'-chloro-4'-methoxyphenoxy) benzoate

The dinitro precursor was prepared by reacting 2-chloro-4-methoxyphenol (Aldrich Chemical Co., Milwaukee, Wis.) as the potassium 2-chloro-4-methoxyphenolate with methyl 4-chloro-3,5-dinitrobenzoate, as desribed in Example 1.2.1. The methyl 3,5-dinitro-4-(2'-chloro-4'-methoxyphenoxy) benzoate product (66% yield) was crystallized from ethanol to give orange crystals. Melting point: 116°–119° C.

Mass Spectrum (EI): M+ in high resolution: calculated for $C_{15}H_{11\,pl}$ $_{ClN2}O_8$, 382.020393; found, 382.020187 (deviation=0.5 ppm).

1.14.2 Methyl 3.5-diiodo-4-(2'-chloro-4'-methoxyphenoxy) benzoate

Since the 2'-chloro substituent in the dinitro precursor is labile with respect to reduction by $H_2$/Pd(C), the precursor was reduced to the 2'-chloro diamine with iron powder in acetic acid/95% ethanol, similarly to Example 1.12. Thus, in a 250 mL flask methyl 3,5-dinitro-4-(2'-chloro-4'-methoxyphenoxy)benzoate (765.5 mg, 2.00 mmol) was dissolved in glacial acetic acid (35 mL) and 95% ethanol (35 mL), the solution heated to 70° C. and iron powder added (2.00 g). The mixture was vigorously swirled in a heating bath (70° C.). After 3 min. of swirling, the mixture developed a brown color. Swirling was continued at 70° C. for 35 min. The mixture was then transferred to a separatory funnel, water (250 mL) and ethyl acetate (250 mL) were added, the product extracted into the ethyl acetate layer, and the ethyl acetate phase allowed to separate from the aqueous phase (3 hours). The extract was dried over anhydrous $Na_2SO_4$, filtered and the ethyl acetate removed by rotary evaporation to yield the crude 3,5-diamino product, which solidified.

The crude diamino product was immediately dissolved in glacial acetic acid (6.0 mL), tetrazotized and converted via the Sandmeyer reaction to methyl 3,5-diiodo-4-(2'-chloro-4'-methoxyphenoxy)benzoate as described in Example 1.2. After purification by preparative thin layer chromatography ($R_f$=0.70) as described in Example 1.2, the product was crystallized from 95% ethanol (250.8 mg off-white crystals, 23% yield). Melting point: 132°–134° C.

Mass spectrum: EI, m/z (relative intensity): 546 (34), 545 (16), 544 (M$^+$, 100), 418 (6), 382 (6). High resolution data for the M$^+$ peak: calculated for $C_{15}H_{11}ClI_2O_4$, 543.843541; found, 543.843424 (deviation=0.2 ppm).

$^1$H NMR spectrum in DMSO-$D_6$ (δ (ppm) values relative to TMS): 3.747 (3H, singlet), 3.881 (3H, singlet), 6.328 (1H, doublet, J=8.97 Hz), 6.780 (1H, doublet of doublets, J=9.10 Hz and J=2.95 Hz), 7.195 (1H, doublet, J=3.02 Hz), 8.400 (2H, singlet).

1.15 Other Compounds

Additional thyroxine analogues described herein can be synthesized using the above-described syntheses from appropriate starting materials, as will be readily apparent to those having skill in the art of organic chemistry. Additional guidance can be found in the art, particularly in Borrows et al., 1949, "The Synthesis of Thyroxine and Related Substances. Part I. The Preparation of Tyrosine and Some of its Derivatives, and a New Route to Thyroxine," *J. Chem. Soc.* 1949 (Supp. Issue No. 1):S185–S190; Borrows et al., 1949, "The Synthesis of Thyroxine and Related Substances. Part II. Preparation of Dinitrophenyl Ethers," *J. Chem. Soc.* 1949 (Supp. Issue No. 1):S190–S199; Clayton et al., 1951, "The Synthesis of Thyroxine and Related Substances. Part VIII. The Preparation of Some Halogeno- and Nitro-diphenyl Ethers," *J. Chem. Soc.* 1951:2467–2473; Gemmill et al., 1956, "3-Iodo-, 3,3'-Diiodo- and 3,3'-Diiodo-5-bromothyroxine," *J. Am. Chem. Soc.* 78:2434–2436; Meltzer et al., 1957, "Thyroxine Analogs," *J. Org. Chem.* 22:1577–1581; Crowder et al., 1958, "Bisbenzylisoquinolines. Part II. The Synthesis of 5-(2-Aminoethyl)-4'-carboxy-2,3-dimethoxydiphenyl Ether," *J. Chem. Soc.* 1958:2142–2149; Jorgensen, 1978, "Thyroid Hormones and Analogues, I. Synthesis, Physical Properties and Theoretical Calculations" In: *Hormonal Proteins and Peptides* Vol. VI, pp. 57–105, C.H. Li, Ed., Academic Press, NY (and references cited therein); and Jorgensen, 1978, "Thyroid Hormones and Analogues, II. Structure-Activity Relationships," In: *Hormonal Proteins and Peptides,* Vol. VI, pp. 107–204, C.H. Li, Ed., Academic Press, NY (and references cited therein).

EXAMPLE 2

Activation of Purified Protein Phosphatase 2A

Compounds 1 and 3, as identified in Table 1, were tested for protein phosphatase 2A activation.

2.1 Preparation of $^{32}$P-labeled Histone H1 Substrate

Histone H1 was phosphorylated with protein kinase C (Upstate Biotechnology, Inc., Lake Placid, N.Y.) in a volume of 100 μL according to standard protocols. Alternatively, histone H1 was phosphorylated with p34cdc2 kinase purified from rapidly multiplying Mytilus Edulis embryos at 4–8 stage after isolation with the p$^{13}$-Suc agarose technique (Smythe and Newport, 1992, "Coupling of Mitosis to the Completion of S Phase in Xenopus Occurs via Modulation of the Tyrosine Kinase that Phosphorylates p34cdc2," *Cell* 68:787–797).

2.2 Phosphatase Assay 125 ng purified protein phosphatase 2A (Upstate Biotechnology, Inc., Lake Placid, N.Y.; Usui et al., 1983, *J. Biol. Chem.* 258:10455–10463) was preincubated with thyroxine analogue (50 μM) in buffer (20 mM MOPS or Tris, pH 7.5, 1 mM MgCl$_2$, 60 μM β-mercaptoethanol) for 10 min. at 23° C. Total reaction volume was 20 μL. $^{32}$P-labeled histone H1 substrate (10 μg, 10$^5$ cpm) was added and the dephosphorylation reaction allowed to proceed for 5 min. at 23° C., after which time the reaction was quenched by addition of 2 μL Laeimli buffer. An identical reaction containing 125 ng untreated protein phosphatase 2A was run as a control.

Phosphorylated and dephosphorylated histone H1 were separated by gel electrophoresis (12% SDS-PAGE), bands containing phosphorylated histone H1 excised and assayed for $^{32}$P activity via scintillation counter.

2.3 Results

The velocity of dephosphorylation in 5 min. is an indication of the initial velocity ($V_{init}$) of the dephosphorylation reaction. $V_{init}$ for compounds 1 and 3 is provided in Table 2, below.

TABLE 2

| Activation of Protein Phosphatase 2A | |
|---|---|
| Thyroxine Analogue | Activity/5 min (cpm) |
| Control | 10217 ± 1708 |
| Compound 1 | 24655 ± 8600 |
| Compound 3 | 7521 ± 1562 |

Reported values are the average of three samples.

These results show that a short (10 min.) preincubation of protein phosphatase 2A with DIME (Compound 1) more than doubles $V_{init}$ of histone H1 dephosphorylation. The 4'-propoxy homologue did not activate protein phoshatase 2A. These data indicate that even minor changes in the ends of the DIME pharmacophore structure (i.e. the methoxy and methyl ester groups) significantly affect activity. These data correlate strongly with protein phosphatase 2A activation observed in in vitro malignant cell assays (see Example 3) and with in vivo anti-tumorigenic efficacy as observed in mice (see Examples 4 and 6).

EXAMPLE 3

Activation of Protein Phosphatase A2 in Tumor Cell Cultures

Compounds 1–13 were tested for protein phosphatase 2A activation in malignant tumor cell cultures in vitro according to the protocol described in Bauer et al., 1996, "Modification of Growth Related Enzymatic Pathways and Apparent Loss of Tumorigenicity of a Ras-Transformed Bovine Endothelial Cell Line by Treatment with 5-Iodo-6-Amino-1,2-Benzopyrone (INH$_2$BP)," *International J. of Oncology* 8:239–252. The results for activation by DIME (Compound 1) are tabulated in Table 3. All other compounds were ineffective.

TABLE 3

| Effect of DIME of the Phosphatase Activity of E-ras 20 Cell Nuclear Extract | |
|---|---|
| | Phosphatase Activity (fmol Pi/mg protein × min.) |
| E-ras nuclear extract (5–10 μg protein per assay) | 29 ± 5 |
| E-ras nuclear extract + 50 μM DIME | 44 ± 7 |
| DU-145 (5–10 μg protein per assay) | 12.1 ± 3 |
| DU-145 + 50 μM DIME | 19.1 ± 2.5 |

Pi= inorganic phosphate

These results demonstrate that 50 μM DIME activates protein phosphatase 2A by at least two-fold in both E-ras transformed bovine endothelial cells and DU-145 cells.

EXAMPLE 4

Cytocidal Action on Human Cancer Cells

The cytocidal action of Compounds 1–13 was tested on seven human cancer cell lines in vitro. DIME (Compound 1)

was maximally active, with the ethoxy derivative (Compound 2) having 25–30% maximal activity.

4.1 Experimental Protocol

Seven human cancer cell lines were obtained from the American Tissue Culture Collection (Rockville, Md.) and maintained in the recommended growth media. Cells were seeded into wells (2 cm$^2$) at a density of 2×10$^4$ cells/cm$^2$. Various concentrations of Compounds 1–13 were added to the media at the time of seeding.

The cultures were incubated for 72 hours at 37° C. (5% CO$_2$ atmosphere). Following incubation, cells were detached with trypsin and counted in a hemocytometer.

4.2 Results

DIME (Compound 1) was maximally active, with the ethoxy analogue (Compound 2) having 25–30% maximal activity. All other analogues tested (Compounds 3–13) were completely inactive.

The experimental results for DIME (Compound 1) are tabulated in Table 4, below. I$_{100}$ designates the concentration at which no viable cells remained; I$_{50}$ the concentration at which 50% viable cells remained, as compared to a control.

TABLE 4

Effect of DIME on Various Human Cancer Cell Lines

| Cell Line | I$_{50}$ ($\mu$M) | I$_{100}$ ($\mu$M) |
| --- | --- | --- |
| HT 144 (melanoma) | 0.5 | 4.0 |
| DU 145 (prostate cancer) | 0.5 | 3.5 |
| HeLA (cervical cancer) | 0.6 | 3.5 |
| HL-60 (promyelocytic leukemia) | 0.6 | 3.0 |
| MDA-MD-231 (mammary cancer) | 0.4 | 3.0 |
| SK-Br-3 (mammary cancer) | 0.6 | 5.0 |
| T47D (ductal mammary cancer) | 0.7 | 3.5 |

EXAMPLE 5

Inhibition of Tumor Cell Growth

Compounds 1 and 14 were tested for inhibition on the growth of MDA-MD-231 cancer cells. Compound 14 exhibited about 25% inhibitory activity as compared to DIME (Compound 1).

5.1 Experimental Protocol

MDA-MD-231 human cancer cells were obtained from the American Tissue Culture Collection (Rockville, Md.) and maintained in the recommended growth media. Cells were grown in the presence of various concentrations of Compounds 1 and 14 for 3 days at 37° C.

5.2 Results

The experimental results are tabulated in Table 5, below.

TABLE 5

Growth Rate of MDA-MD-231 Cells

| Compound 1 ($\mu$M) | Cells (×10$^6$) | Compound 14 | Cells (×10$^6$) |
| --- | --- | --- | --- |
| 0.0 | 0.95 | 0.0 | 0.95 |
| 0.5 | 0.20 | 0.5 | 0.95 |
| 1.0 | 0.10 | 1.0 | 0.71 |
| 2.0 | 0.09 | 2.0 | 0.20 |

The 2'-chloro analogue of DIME (Compound 14) exhibited about 25% inhibitory activity as compared to DIME (Compound 1).

EXAMPLE 6

Loss of Tumorigenicity of E-Ras Transformed Bovine Endothelial Cells

The morphologic action of DIME (Compound 1) was tested in a highly tumorigenic E-ras transformed bovine endothelial cell line.

6.1 Experimental Protocol

E-ras transformed bovine endothelial cells (Bauer et al., 1996, *Intl. J. Oncology* 8:239–252) were exposed to 10 $\mu$M DIME for 3 days. The DIME-treated cells (10$^5$ or 10$^6$ cells/100 $\mu$L) were injected subcutaneously into nude mice and tumor progression followed for 25 days.

6.2 Results

Figure 2:
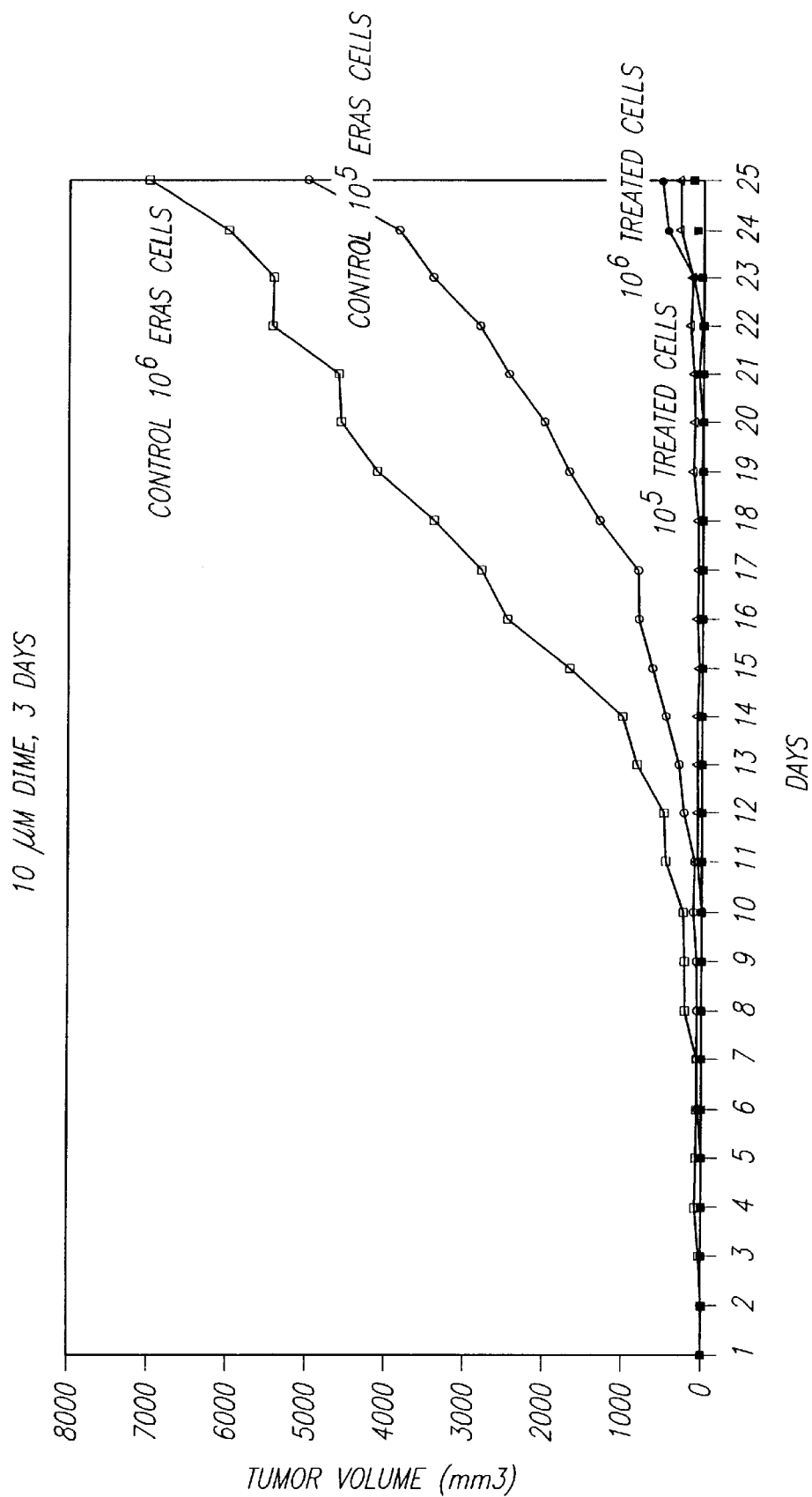
FIG. 2 is a graph illustrating the loss of tumorigenicity of DIME-treated E-ras transformed bovine endothelial cells.

As illustrated in FIG. 1, exposure of E-ras transformed endothelial cells to 10 $\mu$M DIME for a period of 3 days induced extensive micronucleation, coinciding with a loss of tumorigenicity. As illustrated in FIG. 2, animals exposed to non-treated cells exhibited tumor growth (top curves), succumbing to tumors at 25 days. Exposure of cells to 10 $\mu$M DIME prior to injection nearly completely abolished tumorigenicity (lower curves). Tumors did not appear even after 3 months without in vivo drug treatment.

EXAMPLE 7

In Vivo Experiments

The following examples demonstrate the non-toxicity, bioavailability, serum half-life ($t_{1/2}$) and in vivo efficacy of DIME in treating human mammary cancer xenografts in mice.

7.1 Toxicity

Ten nude mice were administered a daily oral dose of $^{14}$C-labeled DIME (Compound 1) (1.0 g/kg, 0.1 mL in corn oil) for a period of 12–15 days. No ill effects were observed in any of the mice during the entire time of treatment.

7.2 Serum Half-Life (t½) and Bioavailability

Mice were orally dosed with 126 mg/kg $^{14}$C-labeled DIME (Compound 1). After dosing, blood sampling times were 15 and 30 minutes and 1, 2, 4, 6, 8 and 24 hours. Aliquots (50 $\mu$L) of blood were assayed in a liquid scintillation counter and data expressed as microgram-equivalents per mL. The blood level data were analyzed by the RSTRIP method (Micromath, Salt Lake City, Utah).

Parallel groups of mice were dosed intravenously with 24.5 mg/kg $^{14}$C-labeled DIME and blood sampling times were 10, 20 and 30 minutes and 1, 2, 4, 6 and 8 hours.

7.2.1 Results

Figure 3:
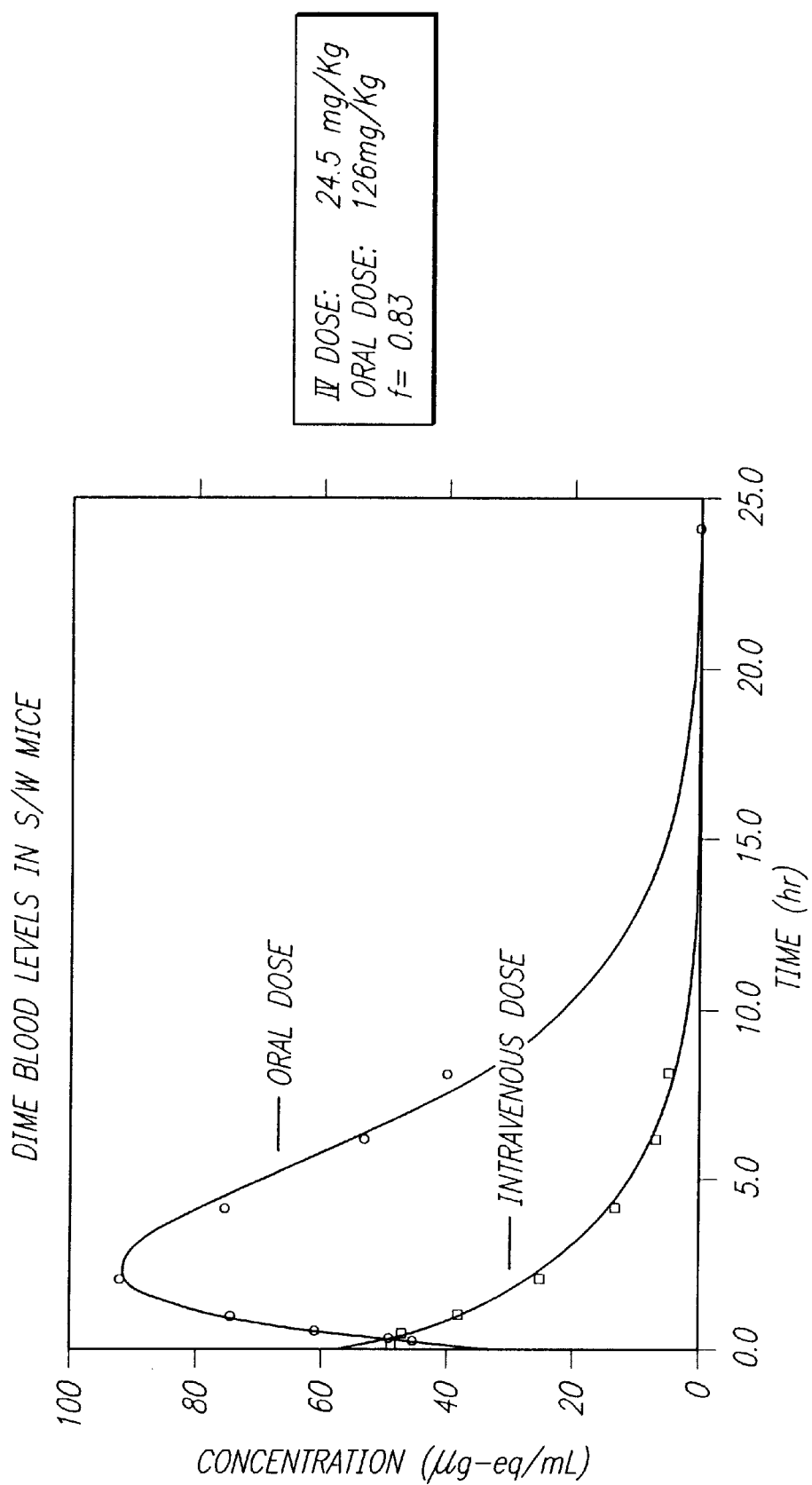
FIG. 3 is a graph illustrating the serum half-life ($t_{1/2}$) and the oral bioavailability of DIME in mice.

The blood serum levels of $^4$C-labeled DIME (mg-eq./mL) are illustrated in FIG. 3. The area under the blood concentration-time curve was 665.28 μg-hr./mL for the oral route (data represented by circles) and 156 μg-hr/mL for the intravenous route (data represented by squares). Bioavailability of orally administered DIME was calculated to be 83% from these data using a standard ratio x dose method. DIME half-life (t½) was about 2–2.5 hours.

7.3 In Vivo Efficacy

The ability of human tumors to grow as xenografts in athymic mice (e.g., nude mice) provides a useful in vivo model for studying the biological response to therapies for human tumors. Since the first successful xenotransplantation of human tumors into athymic mice (Rygaard and Povlsen, 1969, *Acta Pathol. Microbial. Scand.* 77:758–760), many different human tumor cell lines (e.g., mammary, lung, genitourinary, gastrointestinal, head and neck, glioblastoma, bone and malignant melanomas) have been successfully transplanted and grown into nude mice. Human mammary tumor cell lines, including MCF-7, ZR75-1 and MDA-MB-231, have been established as subcutaneous grafts in nude mice (Warri et al., 1991, *Intl. J. Cancer* 49:616–23; Ozzello & Sordat, 1980, "Behaviour of Tumors Produced by Transplantation of Human Mammary Cell Lines in Athymic Nude Mice," *Eur. J. Cancer* 16:553–559; Osbourne et al., 1985, *Cancer Res.* 45:584–590; Siebert et al., 1983, *Cancer Res.* 43:2223–2239).

This experiment demonstrates inhibition of MDA-MB-231 xenografts in nude mice.

7.3.1 Experimental Protocol

MDA-MB-231 (human mammary cancer) cells were obtained from American Type Culture Collection (Rockville, Md.) and maintained in the recommended growth media. Twenty nude mice were each inoculated subcutaneously with MDA-MB-231 cells ($10^6$ cells/100 μL). To one group of ten mice, DIME was administered by gavage (250 mg/kg, 10 mL/kg in corn oil) once per day, 5 days per week, for a total of 32 days. The other (control) group of ten mice was given administered vehicle only according to the same dosing schedule. Tumors were measured twice weekly using a Vernier caliper, and the mean tumor volume was determined at each time point. Comparisons between groups were made using an unpaired, two-tailed t-test and the results were analyzed using analysis of variance.

7.3.2 Results

The average tumor mass at days 14, 21, 28 and 32 post-inoculation for treated and untreated mice is tabulated in Table 5.

TABLE 6

MDA-MB-231 Tumor Volume After DIME Treatment

| Treatment group | Day 14 ± SEM[a] (p value) | Day 21 ± SEM[a] (p value) | Day 28 ± SEM[a] (p value) | Day 32 ± SEM[a] (p value) |
|---|---|---|---|---|
| Control (vehicle) | 284.6 ± 42.0 | 622.2 ± 58.1 | 979.0 ± 154 | 1176.6 ± 222.4 |
| DIME (250 mg/kg) % decrease | 172.0 ± 34.3 (p = 0.06) 40% | 285.7 ± 62.4 (p = 0.02) 54% | 430 ± 85.6 (p = 0.01) 56% | 543.8 ± 122.1 (p = 0.01) 54% |

[a]SEM= standard error of the mean

These data indicate that DIME effects significant reduction of malignant tumor growth, even under a non-optimized treatment regimen.

7.4 In Vivo Efficacy

Other thyroxine analogues described herein are tested as described above. The analogues are expected to exhibit activity according to these assays.

EXAMPLE 8

Formulations

The following examples provide exemplary, not limiting, formulations for administering the thyroxine analogues of the invention to mammalian, especially human, patients. While the examples demonstrate formulations of DIME, it is to be understood that any of the thyroxine analogues described herein may be formulated as provided in the following examples.

8.1 Tablet Formulation

Tablets each containing 60 mg of active ingredient are made up as follows:

| | |
|---|---|
| DIME | 60 mg |
| Starch | 45 mg |
| Microcrystalline Cellulose | 45 mg |
| Sodium carboxymethyl starch | 4.5 mg |
| Talc | 1 mg |
| Polyvinylpyrrolidone (10% in water) | 4 mg |
| Magnesium Stearate | 0.5 mg |
| | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules are dried at 50°–60° C. and passed through a No. 18 mesh U.S. sieve. The sodium carboxymethyl * starch, magnesium stearate and talc, previously passed through a No. 60 mesh U.S. sieve, are then added to the granules, which, after mixing are compressed by a tablet machine to yield tablets each weighing 150 mg.

Tablets can be prepared from the ingredients listed in Table 1 by wet granulation followed by compression.

8.2 Gelatin Capsules

Hard gelatin capsules are prepared using the following ingredients:

| | |
|---|---|
| DIME | 250 mg/capsule |
| Starch dried | 200 mg/capsule |
| Magnesium Stearate | 10 mg/capsule |

The above ingredients are mixed and filled into hard gelatin capsules in 460 mg quantities.

8.3 Aerosol Solution

An aerosol solution is prepared containing the following components:

| | |
|---|---|
| DIME | 0.25% (w/w) |
| Ethanol | 29.75% (w/w) |
| Propellant 22 (Chlorodifluoromethane) | 77.00% (w/w) |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

8.4 Suppositories

Suppositories each containing 225 mg of active ingredient are made as follows:

| | |
|---|---|
| DIME | 225 mg |
| Saturated fatty acid glycerides | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

8.5 Suspensions

Suspensions each containing 50 mg of medicament per 5 mL dose are made as follows:

| | |
|---|---|
| DIME | 50 mg |
| Sodium carboxymethylcellulose | 50 mg |
| Syrup | 1.25 mL |
| Benzoic acid solution | 0.10 mL |
| Flavor | q.v. |
| Color | q.v. |
| Purified water to | 5 mL |

The active ingredient is passed through a No. 45 mesh U.S. sieve and mixed with the sodium carboxymethyl cellulose and syrup to form a smooth paste. The benzoic acid solution, flavor and some color are diluted with some of the water and added, with stirring. Sufficient water is then added to produce the required volume.

EXAMPLE 9

Substitution of an iodine atom for the H atom in position 5 of 6-amino-1,2-benzopyrene significantly augmented the pADPRT inhibitory potency, antiHIV activity and antitumor action of the parent compound. Cole, et al. 1991 "Inhibition of HIV-1 IIIb Replication in AA-2 Cells in Culture by Two Ligands of Poly (ADP-Ribose) Polymerase: 6-Amino-1, 2-benzopyrone and 5-iodo-6-amino-1,2-benzopyrone" *Biochem Biophys. Res. Commun.* 180:504–514; Bauer et al., 1996, "Modification of Growth Related Enzymatic Pathways and Apparent Loss of Tumorigenicity of a ras-Transformed Bovine Endothelial Cell Line by Treatment with 5-iodo-6-amino-1,2-benzopyrone ($INH_2BP$)" *Intl. J. Oncol.* 8:239–252. The question emerged whether or not an increase of the number of iodine substitutions in certain aromatic molecules can modify their molecular pharmacologic properties. As an approach to this question we first analyzed the cellular action of known diiodo-compounds such as thyroid hormone analogs.

It has been established that metabolic or metamorphogenic effects of thyroid hormone analogs depend on their chemical structure. Jorgensen, E. 1978, "Thyroid Hormones and Analogs. II. Structure-Activity Relationships: In Hormonal Protein and Peptides" Vol. VI, Li CH (ed.). Academic Press, New York, pp. 108–203. The hormonally inactive methyl-3,5-diiodo-4-(4'-methoxyphenoxy) benzoate (DIME) was first synthesized in 1949 (Borrows, et al. 1949, "The Synthesis of thyroxine and Related Substances. Part I. The Preparation of Tyrosine and Some of its Derivatives, and a New Route to Thyroxine", *J. Chem. Soc. Suppl. Issue No.* 1:S185–S190) but no significant metabolic or metamorphogenic action of this substance has been reported, Money et al. 1958, "The Effect of Change in Chemical Structure of Some Thyroxine Analogues on the Metamorphosis of Rana pipiens Tadpoles", *Endocrinology* 63:20–28; Stasili et al., 1959, "Antigoitrogenic and Calorigenic Activities of Thyroxine Analogues in Rats", *Endocrinology* 64:62–82; Money et al., 1959, "The Effect of Various Thyroxine Analogues on Suppression of $^{131}I$ Uptake by the Rat Thyroid", *Endocrinology* 64:123–125; Kumaoka et al., 1960, "The Effect of Thyroxine Analogues on a Transplantable Mouse Pituitary Tumor", *Endocrinology* 66:32–38; Grinberg et al., 1962, "Studies with Mouse Pituitary Thyrotropic Tumors. V. Effect of Various Thyroxine Analogs on Growth and Secretion", *Cancer Res.* 22:835–841. In work commenced earlier by the inventors DIME has been shown as a potential tumoricidal agent both in cell cultures and in vivo. Kun et al., 1996, "Induction of Tumor Apotosis by methyl-3,5-diiodo-4-(4'-methoxyphenoxy) benzoate (DIME)", Abstract No. 102, *Int. J. Oncol.* 9:supplement 829; Zhen, et al., 1997, "Induction of Metaphase Block and Endoreduplication in Human Cancer Cells" by 3,5-diiodo-4(4'-methoxyphenoxy) benzoate (DIME). Abstract, Amer. Assoc. *Cancer Res.*, Symposium on Cell Signaling and Cancer Treatment, Telfs-Buehen, Austria, February 23–28, 1997. Synthesis and testing of structural homologs and analogs of DIME, differing only in the side chain substitutions, as shown in copending U.S. patent application. Ser. No. 08/655,267, filed Jun. 4, 1996, "Method of Treating Malignant Tumors with Thyroxine Analogs having No Significant Hormonal Activity", delineated the structural specificity for tumoricidal activity of DIME.

The following work shows the structure-action comparison of DIME and 17 of its analogs, and describes the tumoricidal action of DIME itself at a cellular level. Drug metabolism and cellular uptake assays with DIME indicated the reasons for the lack of its animal toxicity in vivo. Cytometric analysis of the mode of action of DIME and biochemical mechanisms are the subjects of consecutive studies.

Substituted phenols for the synthesis of compounds 1–4 and 10–18 in Table 1 were obtained for Aldrich Chemical Co. (Milwaukee, Wis., USA). Methyl-4-chloro-3,5-dinitrobenzoate, Ullmann F, 1909, "die 4-chlor-3,5-dinitrobenzoesaure", *Annalen der* Chemie 36:92–93; was prepared from 4-chloro-3,5-dinitrobenzoid acid (Aldrich).

9.1 General Synthesis

Each substituted phenol (as its potassium phenolate) was reacted with methyl-4-chloro-3,5-dinitrobenzoate to give the methyl-3,5-dinitro-4-(Substituted phenoxy) Benzoate, which was then reduced to the corresponding 3,5-diamine and converted to the target 3,5-diodo compound by the Sandmeyer reaction. Kun et al., 1996, "Induction of Tumor Apotosis by methyl-3,5-diiodo-4-(4'-methoxyphenoxy) benzoate (DIME)", Abstract No. 102, *Int. J. Oncol.* 9:supplement 829. Generally the reduction was by catalytic hydrogenation, but for cases where $R_1$ or $R_3$ is a halogen atom (compounds 12 and 14) reduction was by iron powder in acetic acid/ethanol to avoid dehalogenation. Kun et al., 1996, "Induction of Tumor Apotosis by Methyl-3,5-Diiodo-4-(4'-Methoxyphenoxy) Benzoate (DIME)", Abstract No. 102, *Int. J. Oncol.* 9:supplement 829. Purification was generally by preparative thin layer chromatography and crystallization. For compounds where $R_2$ in Table 7 is other than methoxy (viz. compounds 5–9), additional synthesis reactions were employed. Compound 6 was prepared by base hydrolysis of compound 1. Borrows, et al. 1949, "The Synthesis of Thyroxine and Related Substances. Part I. The Preparation of Tyrosine and Some of its Derivatives, and a New Route to Thyroxine", *J. Chem. Soc.* Suppl. Issue No. 1:S185–S190. Compounds 5, 8 and 9 were prepared by reaction of the acid chloride of 6, Borrows, et al. 1949, "The Synthesis of Thyroxine and Related Substances. Part I. The Preparation of Tyrosine and Some of its Derivatives, and a New Route to Thyroxine", *J. Chem. Soc.* Suppl. Issue No. 1:S185–S190; with anhydrous ethanol, methylamine and dimethylamine respectively. Kun et al., 1996, "Induction of Tumor Apotosis by methyl-3,5-diiodo-4-(4'-methoxyphenoxy) Benzoate (DIME)", Abstract No. 102, *Int. J. Oncol.* 9:supplement 829. Compound 7 was obtained by reaction of 1 with ammonia in anhydrous methanol. All compounds were characterized by melting point and high-resolution mass spectrometry (Table 7), with the exception of the known carboxylic acid 6. $^1$H NMR spectra were measured for compounds 1–14 and were satisfactory in all cases.

TABLE 7

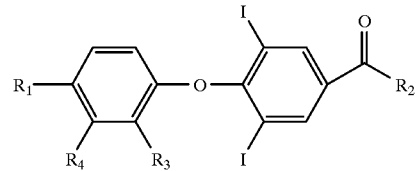

| Comp. No. | R1 | R2 | R3 | R4 | M.P. °C. | Formula | Calcd. | Found |
|---|---|---|---|---|---|---|---|---|
| 1 | CH$_3$O | CH$_3$O | H | H | 153—155 | C$_{15}$H$_{12}$I$_2$O$_4$ | 509.882513 | 509.882960 |
| 2 | EtO | CH$_3$O | H | H | 123–125 | C$_{16}$H$_{14}$I$_2$O$_4$ | 523.898163 | 523.898737 |
| 3 | n-PrO | CH$_3$O | H | H | 114–116 | C$_{17}$H$_{16}$I$_2$O$_4$ | 537.913813 | 537.914014 |
| 4 | n-BuO | CH$_3$O | H | H | 82–84 | C$_{18}$H$_{18}$I$_2$O$_4$ | 551.929463 | 551.930000 |
| 5 | CH$_3$O | EtO | H | H | 96–98 | C$_{16}$H$_{14}$I$_2$O$_4$ | 523.898163 | 523.898202 |
| 6 | CH$_3$O | HO | H | H | 233–235 | C$_{14}$H$_{10}$I$_2$O$_4$ | a | |
| 7 | CH$_3$O | H$_2$N | H | H | 207–209 | C$_{14}$H$_{11}$I$_2$NO$_3$ | 494.882847 | 494.881880 |
| 8 | CH$_3$O | (CH$_3$)HN | H | H | 181–183 | C$_{15}$H$_{13}$I$_2$NO$_3$ | 508.898497 | 508.898971 |
| 9 | CH$_3$O | (CH$_3$)$_2$N | H | H | 162–164 | C$_{16}$H$_{15}$I$_2$NO$_3$ | 522.914148 | 522.914364 |
| 10 |  | CH$_3$O | H | H | 204 dec. | C$_{14}$H$_{10}$I$_2$O$_4$ | 495.966963 | 495.867453 |
| 11 |  | CH$_3$O | H | H | 142–144 | C$_{14}$H$_{10}$I$_2$O$_3$ | 479.871948 | 479.872553 |
| 12 |  | CH$_3$O | H | H | 139–141 | C$_{14}$H$_9$I$_3$O$_3$ | 605.768600 | 605.767839 |
| 13 |  | CH$_3$O | H | CH$_3$O | 123–125 | C$_{15}$H$_{12}$I$_2$O$_4$ | 509.882513 | 509.882387 |
| 14 | CH$_3$O | CH$_3$O | Cl | H | 132–134 | C$_{15}$H$_{11}$ClI$_2$O$_4$ | 543.843541 | 543.843424 |
| 15 | CH$_3$O | CH$_3$O | H | CH$_3$O | 189–192 | C$_{16}$H$_{14}$I$_2$O$_5$ | 539.893078 | 539.893930 |
| 16 |  | CH$_3$O | H | H | 116–119 | C$_{16}$H$_{14}$I$_2$O$_3$ | 507.903248 | 507.903425 |
| 17 |  | CH$_3$O | H | H | 125–128 | C$_{15}$H$_{12}$I$_2$O$_3$ | 493.887598 | 493.886936 |
| 18 | CF$_3$O | CH$_3$O | H | H | 94–97 | C$_{15}$H$_9$F$_3$I$_2$O$_4$ | 563.854248 | 563.855633 |

$^a$Elemental analysis previously reported in Borrows et al., J. Chem. Soc. 1959, S185–S190.

9.2 Synthesis of Compound 1

Synthesis of Compound 1 (DIME) was performed as earlier described by Borrows, et al. 1949, "The Synthesis of thyroxine and Related Substances. Part I. The Preparation of Tyrosine and Some of its Derivatives, and a New Route to Thyroxine", *J. Chem. Soc.* Suppl. Issue No. 1:S185–S190, m.p. 153°–155° C. Fundamental spectral measurements, previously not reported for this compound, are as follows. UV absorption spectrum in ethanol, τ max(ε): 289 nm (4.20×10$^3$), 232 nm (3.08×10$^4$), 213 nm (2.48×10$^4$). Mass spectrum: FAB, m/z (relative intensity): 510 (M$^+$, 100), 479 (4.5), 384 (4.5). High-resolution data for the M$^+$ peak: calculated for C$_{15}$H$_{32}$I$_2$O$_4$, 509.882513; found, 509.882960 (deviation=–0.9 ppm). 1H NMR spectrum in DMSO-d6 (δ(ppm) values relative to TMS): 3.719 (3H, singlet), 3.876 (3H, singlet), 6.693 (2H, doublet, J=9.45 Hz, plus fine-splitting), 6.845 (2H, doublet, H=9.36 Hz, plus fine-splitting), 8.390 (2H, singlet).

9.3 Synthesis of Compound 7

Synthesis of Compound 7 (3,5-diiodo-4-(4'methoxyphenoxy) benzamide) was achieved by bubbling ammonia into a solution of compound 1 (100 mg, 0.196 mmole) in anhydrous methanol (60 ml) at ambient temperature for 5 min. After standing 1 hr. in a stoppered flask, the mixture was treated again with ammonia and then allowed to stand stoppered for 48 hours. The methanol/ammonia was removed by rotary evaporation, the dry residue dissolved in warm methanol:water (7:3 v/v)(30 ml) and crystallized in the refrigerator (3° C.). Yield: 58.3 mg (60%) of buff-colored crystals, m.p. 207°–209° C. Mass spectrum (FAB): High-resolution data for the M$^+$ peak: calculated for $C_{14}H_{11}I_2NO_3$, 494.882847; found, 494.881880 (deviation= 2.0 ppm). $^1$H NMR spectrum in DMSO-d6 (δ (ppm) values relative to TMS): 3.716 (3H, singlet), 6.682 (2H, doublet, J=8.93 Hz, plus fine-splitting), 6.895 (2H, doublet, J=8.99 Hz, plus fine-splitting), 7.528 (1H, singlet), 8.113 (1H, singlet), 8.402 (2H singlet).

9.4 Cell Cultures

E-ras 20 cells were cultured as reported, Bauer et al., 1996, "Modification of growth related enzymatic pathways and apparent loss of tumorigenicity of a ras-transformed bovine endothelial cell line by treatment with 5-iodo-6-amino-1,2-benzopyrone (INH$_2$BP)" *Intl. J. Oncol.* 8:239–252; HT-144 (melanoma), DU-145 (prostatic cancer), HeLa (cervical cancer), HL 60 (promyelocytic leukemia), MDA-MB-231 (mammary cancer), SK-Br-3 (mammary cancer), T47D (ductal mammary cancer), A559 (lung cancer) were obtained from American Type Culture Collection (Rockville, Md.) and cultured in prescribed media. The effect of DIME was tested in cultures with a starting cell density of $2 \times 10^4$ cells per cm$^2$ and comparison of the effect of DIME on cell growth (intact cells identified by Trypan blue exclusion) was assayed by direct cell counting after trypsinization in a hemocytometer 72 hours after drug addition.

9.5 Tumorigenicity of E-ras 20 Cells

Tumorigenicity of E-ras 20 Cells in athymic nude mice was assayed as described previously. Bauer et al., 1996, "Modification of growth related enzymatic pathways and apparent loss of tumorigenicity of a ras-transformed bovine endothelial cell line by treatment with 5-iodo-6-amino-1,2-benzopyrone (INH$_2$BP)" *Intl. J. Oncol.* 8:239–252. The in vivo antitumorigenic action of DIME was assayed on athymic mice inoculated with $10^6$ MDA-MB-231 cells, as in the tumorgenicity assay. In about 10–14 days when subcutaneous tumors appeared, DIME treatment consisting of p.o. administration of DIME suspension (once a day) was commenced and continued for 28–32 days as reported, Kun et al., 1996, "Induction of tumor apotosis by methyl-3,5-diiodo-4-(4'-methoxyphenoxy) benzoate (DIME)", Abstract No. 102, *Int. J. Oncol.* 9:supplement 829.

9.6 Assays for Quantitation of Colony Formation

Assays for Quantitation of colony formation were performed as reported, Vidair, et al., 1986 "Evaluation of a Role for Intracellular Na$^+$, K$^+$, Ca$^{2+}$ and Mg$^{2+}$ in hyperthermic cell killing" *Radiation Res.* 105:187–200.

9.7 DIME-Sepharose Affinity Column.

EAH-Sepharose (Pharmacia, Piscataway, N.J., USA) (2.0 g wet) was washed with water and solvent exchanged into 60% DMF (aq). The wet cake was resuspended in 60% DMF (1.0 ml) containing the carboxylic acid derivative of DIME (compound 6) (60 mg) and a 10-fold excess of N,N$^1$-dicylohexycarbodiimide (Sigma) and the suspension was gently rotated at ambient temperature for 16 hours. The Sepharose beads were then collected on a sintered glass filter and sequentially washed with DMF, dioxane, DMF, aqueous DMF (66%, 50% and 33%) and finally with water. Based on the UV absorption spectrum of the substituted beads, the content of DIME-groups was in the range of 1–2 gmol per ml of damp cake.

9.8 Metabolism of [$^{14}$C]-DIME.

(a) mouse tissue homogenate (brain, kidney, liver lung) consisting of 0.2 g of tissue in 1.0 ml. of homogenization buffer (50 mM Tris (pH 7.4), 400 mM NaCl, 10 mM MgCl$_2$, 1 mM EDTA, 0.5% NP-40, 0.5 mM PMSF) each were combined with 1.0 ml of MES buffer (100 mM ph 6.5) containing 20 μM [$^{14}$C]-DIME (10.55 mCi/mmol), and the mixtures were incubated at 37° C. for 4 hours. Then to each tube was added sequentially ethyl acetate (1.5 ml), ammonium sulfate (900 mg) and 60% perchloric acid (160 μl), with vortexing after each addition. After standing for 10 minutes, phase separation was enhanced by benchtop centrifugation. The upper (ethyl acetate) layer was drawn off, and the lower aqueous and interphase material was extracted with a second portion of ethyl acetate (1.5 ml). The ethyl acetate extracts (combined) contained more than 90% of the total cpm present in the original incubate (ca. $4 \times 10^5$ cpm). The extracts were evaporated to dryness using a stream of N$^2$, the respective residues taken up in ethyl acetate (100 μl) and aliquots (10 μl) spotted on analytical silica-gel TLC plates (Whatman PE SIL G/UV flexible plates 250 μm thickness, 10 cm×20 cm) and developed with 3:1:0.8 v:v:v n-hexane/ethyl acetate/ethanol. Analyte bands, including [$^{14}$C]-DIME as reference standard, were visualized by autoradiography. Additional reference standards (nonradioactive DIME and its carboxylic acid analog) were visualized on the plates under UV light. (b). Metabolism of [$^{14}$C]-DIME in cells in culture: Cells ($2–5 \times 10^6$ in each test) were incubated with [$^{14}$C]-DIME, then homogenized and assayed for metabolites as in (a).

9.9 Intracellular Concentration of DIME.

Monolayer cultures in 9.6 cm$^2$ wells (3 ml medium) were exposed to [$^{14}$C]-DIME (10.55 mCi/mmol) for 24 hours, then washed 7 times with 1 ml medium containing unlabeled DIME. The cells were dissolved in 1 ml of 4% Na$_2$CO$_3$ and 0.2 M NaOH and radioactivity measured by scintillation counting. Cell volume was determined by hematocrit and cell counting from parallel wells treated with unlabeled DIME.

9.10 Assay for DNA Cuts

Assay for DNA cuts, as a signal for apoptosis, was via the terminal deoxynucleotidyl transferase dUTP nick end labeling (TUNEL) reaction as specified by the manufacturer of the assay kit (Boehringer Mannheim, Indianapolis, Ind., USA, Cat. No. 168–4817).

9.11 Results

The carboxyl-esterase inhibitor bis[p-nitrophenyl] phosphate (BNPP), Heymann, et al., 1968, "Inhibition of phenacetin and acetanilide-induced methemoglobinemia in the rat by the carboxyl esterase inhibitor of bis[p-nitrophenyl] phosphate", Biochem. Pharmacol. 18:801–811, was obtained from Sigma.

The structural specificity of DIME and its homologs and analogs can be assessed by examining Table 7 and Table 8. We have prepared 17 novel structural analogs of DIME and compared the antitumor activity of 10 of the compounds (Table 8) which appears sufficient to draw some general conclusions. The biological assay chosen was the determination of antitumorigenic action of the drugs on the in vivo tumorigenicity of E-ras cells in nude mice, Bauer et al., 1996, "Modification of growth related enzymatic pathways and apparent loss of tumorigenicity of a ras-transformed bovine endothelial cell line by treatment with 5-iodo-6-amino-1,2-benzopyrone (INH$_2$BP)" Intl. J. Oncol. 8:239–252. E-ras 20 cells ($10^5$ or $10^6$) were incubated with 10 μM DIME or analogs for 4 days, then $10^5$ and $10^6$ cells were inoculated subcutaneously into nude mice (5 per test) and rates of tumor formation quantitated by direct tumor volume measurements (cf. 2). As shown for DIME itself (FIG. 4) tumor formation was completely abrogated. Identical antitumorigenic tests were performed with nine DIME analogs and taking the effect of DIME as 100% (comparing tumor sizes at day 25) the antitumor efficacy was calculated as percent of DIME activity. It should be noted that E-ras 20 cells are relatively less sensitive to DIME than human tumors, therefore these results serve only a basis for comparison of DIME analogs. Results summarized in Table 8 illustrate that substituents in $R_1$ and $R_2$ determine antitumor efficacy. This effect is particularly striking when comparing $R_1CH_3O$, EtO, n-Pro, nBuO in $R_1$, suggesting that side chain parameters, not the binding of the "thyroxine-like" core structure itself, appear to confer pharmacological specificity.

This conclusion is substantiated by preliminary protein binding studies with the DIME-Sepharose affinity column. In this affinity column DIME was covalently bound to a matrix at $R_2$, therefore this DIME derivative, by analogy to the results in Table 8, would have significantly less tumoricidal action than DIME, (See, Kun et al. U.S. patent application. Ser. No. 08/655,267, filed Jun. 4, 1996, "Method of treating malignant tumors with thyroxine analogs having no significant hormonal activity" the disclosure of which is incorporated herein by reference. Yet percolation of cell extracts through this column resulted in protein binding to the affinity matrix; one of the absorbed proteins was identified as tubulin. Protein binding of DIME was determined by the centricon method as reported previously, Bauer et al., 1996, "Modification of growth related enzymatic pathways and apparent loss of tumorigenicity of a ras-transformed bovine endothelial cell line by treatment with 5-iodo-6-amino-1,2-benzopyrone (INH$_2$BP)" Intl. J. Oncol. 8:239–252. Calculated from Scatchard plots $k_D$ values of $10^9$ to $10^{10}$ were obtained with proteins present in cell extracts, even with BSA, indicating a presumably hydrophobic association of DIME with various proteins. Based on results with the DIME-Sepharose affinity column, we attribute this binding to the "core" structure of DIME.

TABLE 8

Inhibition of E-ras 20 tumorigenicity: efficacy of DIME and some structural analogs

| Compound NO.$_a$ | Efficacy (%) |
|---|---|
| 1 | 100 |
| 2 | 93 |
| 5 | 83 |
| 9 | 64 |
| 7 | 53 |
| 6 | 45 |
| 3 | 44 |
| 8 | 22 |

TABLE 8-continued

Inhibition of E-ras 20 tumorigenicity: efficacy of DIME and some structural analogs

| Compound NO.$_a$ | Efficacy (%) |
|---|---|
| 10 | 14 |
| 4 | 4 |

The efficacy of DIME analogs on in vivo tumorigenicity of E-ras 20 cells in athymic mice was compared to that of DIME (compound 1) which was taken as 100, determining the size of tumor reduction at day 25. Pretreatment with DIME or its analogs (Table 7) was with 10 μM for 4 days prior to s.c. innoculation.
$_a$as assigned in Table 7.

The relative activities of DIME analogs can be deduced from Table 8, however the present experiments focused primarily on the cytocidal action of DIME itself in order to define experimental systems suitable for more detailed analyses of DIME analogs. Extending the antitumorigenic action of DIME (FIG. 1) to in vivo conditions, it is shown that feeding of DIME to nude mice produces 70–85% tumor regression in 25–35 days by daily doses per os of 0.25 to 1.0 g/kg, Kun et al., 1996, "Induction of tumor apotosis by methyl-3,5-diiodo-4-(4'-methoxyphenoxy) benzoate (DIME)", Abstract No. 102, Int. J. Oncol. 9:supplement 829. These large doses produced no noticeable toxicity for the probable reason described below. Since 0.25 g/kg and 1.0 g/kg DIME had the same antitumor effect a dose-response relationship was not apparent. This paradox may be explained by a selective drug uptake into tumor cells in vivo as discussed.

In the present study we focused on microscopic methods of analyses of cell killing. As illustrated in FIG. 5, colony forming ability of MDA-MB-231 cells was profoundly diminished by DIME in a concentration range of 1–2 μM in 10 days. When DIME was removed prior to the end of 8 hours incubation with cells, cell killing was prevented and drug-induced morphologic changes were completely reversed. Replating cells washed free of DIME up to 8 hours following preincubation with 1–10 μM DIME resulted in a restarting of normal cell growth and replication. The nature of critical events that after 8 hours of drug treatment produce an irreversible path leading to cell death are as yet unknown, and is the subject of further studies. However, one of the readily detected causes of ultimate cell death induced by DIME is drug concentration-dependent DNA breaks as illustrated in FIG. 6.

A striking property of DIME is its apparent selectivity for tumors in vivo. We performed drug metabolism and cellular DIME uptake tests to further characterize this property. Incubation of cells in culture with [$^{14}$ DIME, under conditions described previously, Bauer et al., 1996, "Modification of growth related enzymatic pathways and apparent loss of tumorigenicity of a ras-transformed bovine endothelial cell line by treatment with 5-iodo-6-amino-1,2-benzopyrone (INH$_2$BP)" Intl. J. Oncol. 8:239–252, resulted in cellular uptake of the drug into a form which cannot be washed out from cells with PBS containing nonradioactive DIME present at the same concentration added extracellulary during incubation (cf. 2). The rate of drug uptake is significantly higher in cells (e.g., MDA-MP-231) which are most readily killed by DIME as compared to less DIME-sensitive cells (Table 9). We developed a transformed phenotype of the normal kidney cell, CV-1 cells, which exhibit a loss of contact inhibition and rapid doubling time (12 hours vs. 54 hours of nontransformed phenotype). As shown in Table 9 the tumorigenic transformed cells in general took up DIME more rapidly than nontransformed cells (CV-1) or cells that were less sensitive to killing-by DIME (e.g. E-ras 20). Established cell lines have undergone immortality crisis, thus not strictly physiologically operating cells, and our drug uptake results and the apparent lack of DIME toxicity in vivo suggest that normal cells in the intact animal may take up no or very little DIME. On the other hand homogenates of organs of normal mice actively metabolize (de-esterify) DIME as illustrated in Table 10. The highest rate of "DIME-esterase" activity occurred in brain homogenates.

TABLE 9

Uptake of DIME

| Cell type | Extracellular DIME$_{a,b}$ | Intracellular DIME$_a$ |
|---|---|---|
| E-ras 2- (24 hours) | 10 | 105 ± 20, (n = 4) |
| MDA-MB-231 (24 hours) | 2 | 120 ± 15, (n = 4) |
| CV-1 (24 hours) | 2 | 25 ± 4, (n = 3) |
| CV-1-Transformed (24 hours) | 2 | 66 ± 6, (n = 3) |

Cellular concentration of DIME by four cell types following incubation for 24 hours (see Methods).
$_a\mu M$;
$_b$The concentration of DIME was chosen that causes 100% growth inhibition, leaving 20 to 50 × 10$^4$ attached cells/cm$^2$.

TABLE 10

Esterase cleavage of DIME to its carboxylic acid$^a$ in various tissue homogenates

| Tissue | [$^{14}$C-DIME$^b$] | [$^{14}$C]-acid$^{a, b}$ |
|---|---|---|
| Brain | 14.9 (305,000 cpm) | 3.6 (73,800 cpm) |
|  | 17.1 (350,000 cpm) | 2.0 (41,250 cpm) |
| Liver | 186. (381,000 cpm) | 1.4 (27,900 cpm) |
| Lung | 19.4 (396,000 cpm) | 1.0 (20,500 cpm) |

$^a$Compound 6 in Table 7.
$^b$In nmol, isolated by thin layer chromatography, starting from 20.0 mol of [$^{14}$C]-DIME incubated in 2.0 ml of homogenate at 37° C. for 4 hours. Cpm values have a variability of ±2%. The specific radioactivity of the [$^{14}$C]-DIME was 20,470 cpm/nmol.

Figure 4:
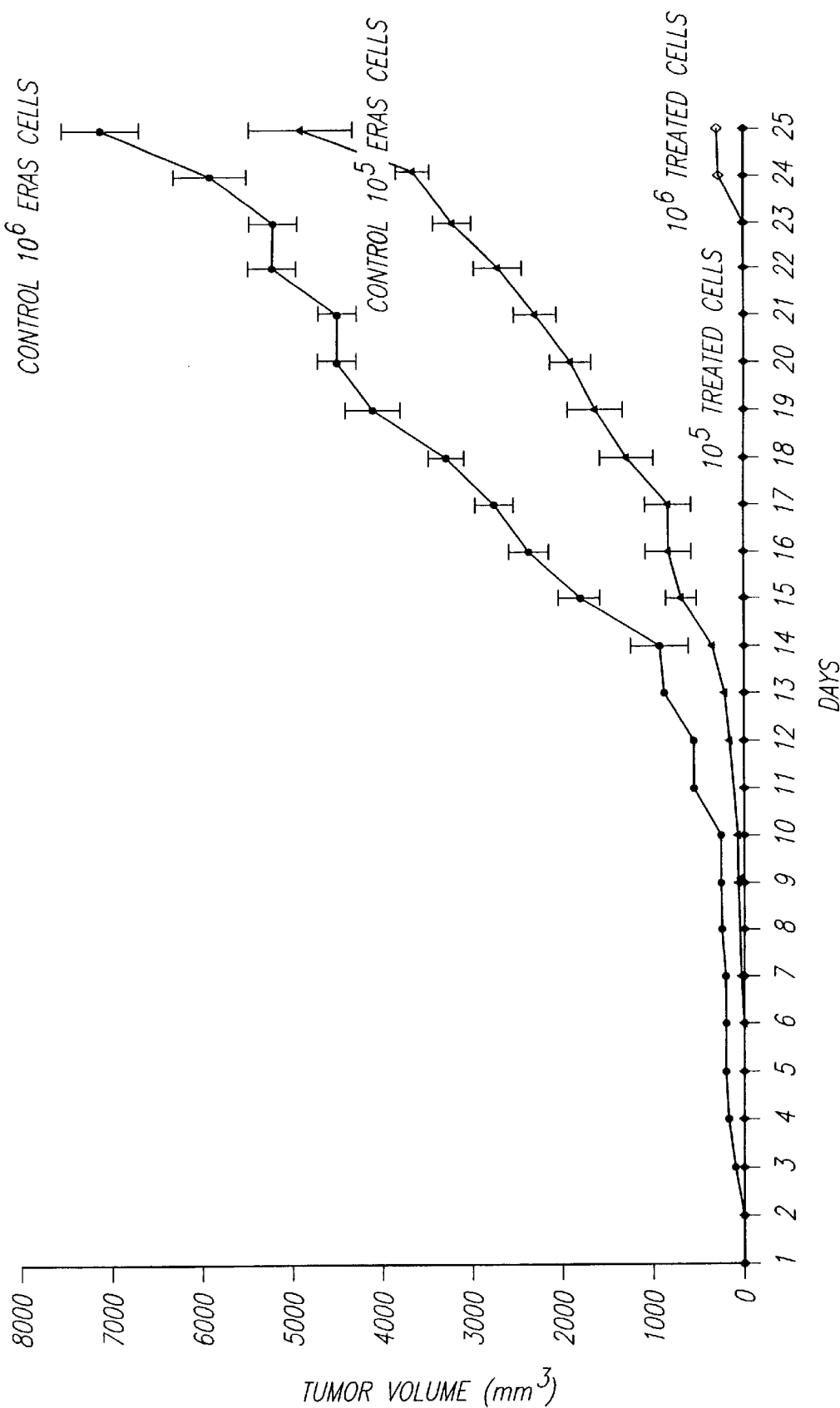
FIG. 4 shows the submorigenic effect of DIME (10 μM for 4 days) pretreatment of the tumor formation from $10^5$ or $10^6$ E-ras 20:cells per inoculum.
Figure 6A:
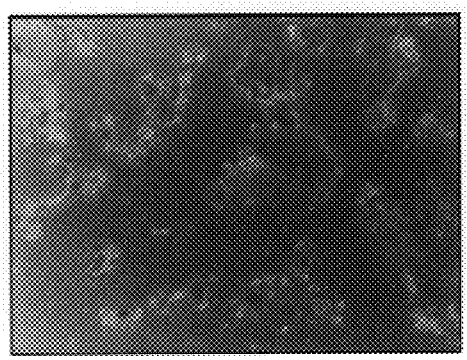
FIG. 6 shows the induction of DNA breaks by 0.0 μM(a), 2.0 μM(b), 5 μM(c) and 10 μM(d). E-ras cells (2×$10^4$ cells/cm$^2$) were treated with DIME 18 hours prior to the TUNEL assay.
Figure 6B:
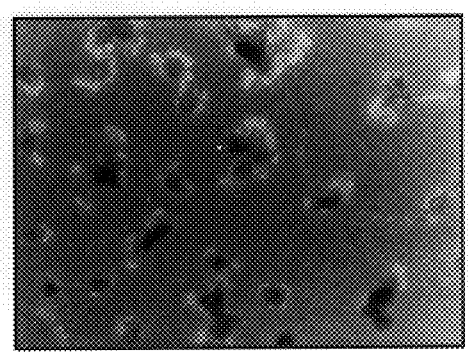
Figure 6C:
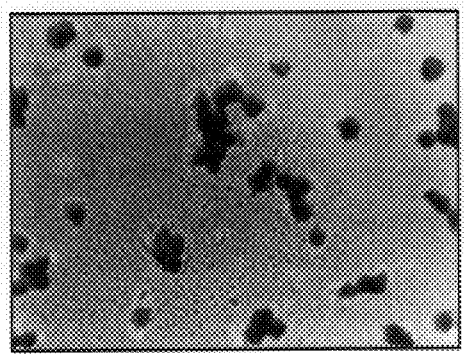
Figure 6D:
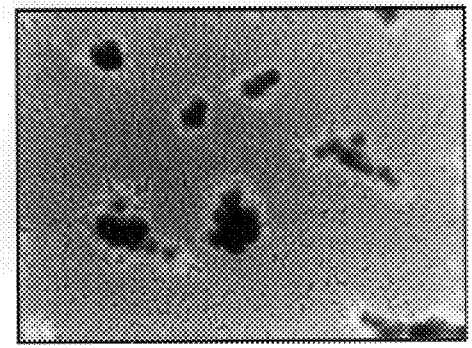
Figure 7:
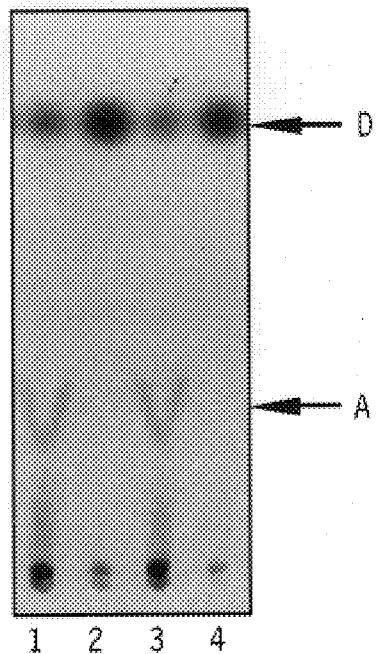
FIG. 7 shows the separation by thin layer chromatogray of DIME (D) and its carboxylic acid (A) degradation product by A-549 (lung cancer) cell extracts (equivalent to 2×$10^6$ cells). In the experiment shown in lines 1 and 2 the esterase activity of the extract occurs during 4 hours incubation with 1 μM DIME. Line 2 illustrates the esterase inhibition by 125 μM BNPP. Lines 3 and 4 depict the same experiments as in lines 1 and 2, except the cell extracts were prepared from intact cells preincubated for 24 hours with 1 μM DIME, then washed and extracted. This experiment illustrates that the esterase is not induced by DIME.
Figure 8:
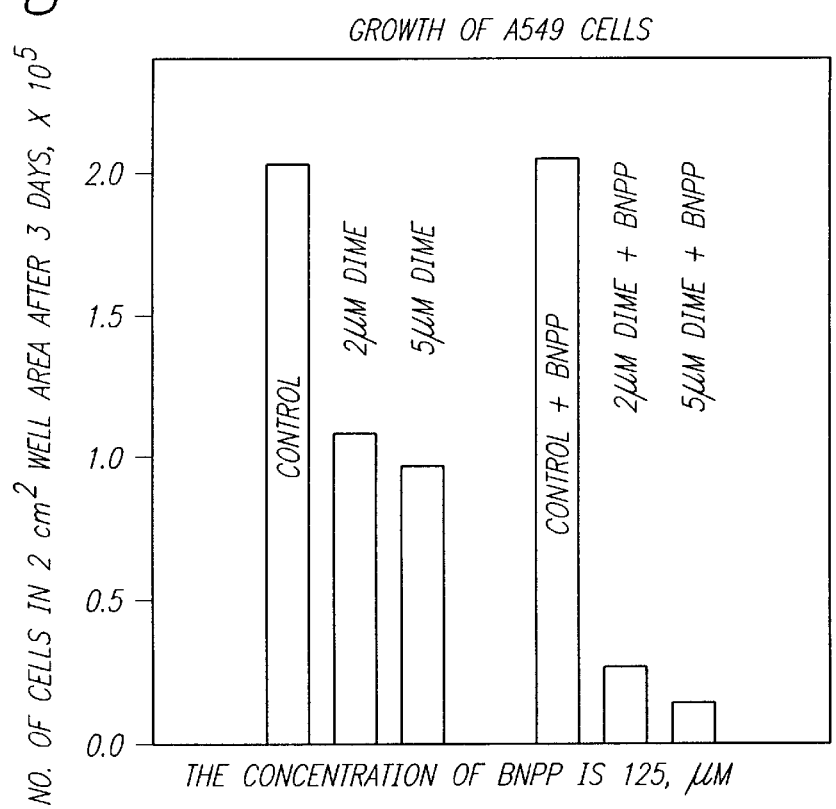
FIG. 8 shows the augmentation of the inhibitory action of DIME on the growth of A-59 cells by BNPP.
Figure 9:
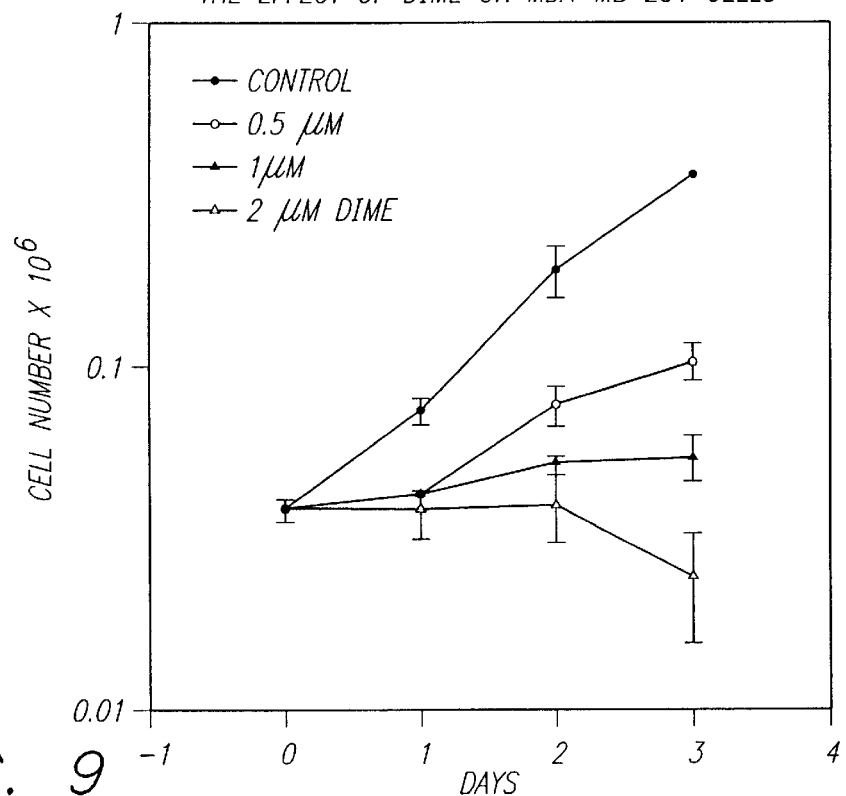
FIG. 9 graphs the effect of DIME on MDA-MB231 cells. Initial seeding density was 0.05×$10^6$ per 2 cm$^2$.

Correlation of drug metabolism and tumoricidal action of DIME was also demonstrated in experiments with human lung tumor cells (A-549). As shown in FIG. 4, A-549 cells readily cleave the ester bond (R$_2$) in DIME whereas inhibiting esterase activity with bis[p-nitrophenyl] phosphate, Heymann, et al., 1968, "Inhibition of Phenacetin and Acetanilide-Induced Methemoglobinemia in the Rat by the Carboxyl Esterase Inhibitor of bis[p-Nitrophenyl) Phosphate", Biochem. Pharmacol. 18:801–811, resulted in much more effective cell killing by DIME on A-549 cells, as seen in Figure V. A comparison of the cell growth inhibitory action of DIME on various cancer cells, expressed in DIME concentration that causes 50% cell arrest in 3 days, is summarized in Table 11. A time course of the action of DIME at 0.5, 1.0 and 2.0 $\mu$M final concentration on MDA-MB-231 cells is illustrated in FIG. 6.

TABLE 11

Effect of DIME on various human cancer cell lines

| Cell line | I$_{50}$, $\mu$M (day 3) |
|---|---|
| E=ras 20 | 1.0 |
| LHT 144 (melanoma) | 0.5 |

TABLE 11-continued

Effect of DIME on various human cancer cell lines

| Cell line | I$_{50}$, $\mu$M (day 3) |
|---|---|
| DU 145 (prostate cancer) | 0.5 |
| HeLa (cervical cancer) | 0.6 |
| HL 60 (promyelocytic leukemia) | 0.4 |
| MDA-MB-231 (mammary cancer) | 0.4 |
| SK-Br-3 (mammary cancer) | 0.6 |
| T47D (ductal mammary cancer) | 0.7 |

For DIME-exposure experiments cells were seeded into 2 cm$^2$ wells at a density of 2×10$^4$ cells/cm$^2$. DIME at various concentrations was added to the medium at the time of seeding. The cell cultures were then incubated for 3 days (37° C. in 5% at CO$_2$ atmosphere).

DIME is a unique tumoricidal molecule inasmuch as it appears to have no macroscopically observed toxicity in vivo except for tumor cells growing in intact animals. From drug uptake assays it seems apparent that cells that are sensitive to cell killing by DIME take up the drug most avidly. Replication of noncancer cells growing in cultures is also inhibited to varying degrees by DIME (not shown), whereas the drug does not show toxicity in vivo. Therefore it appears probable that the permeability of cells to DIME in cell cultures differs from cells functioning in vivo. The reasons for this apparent tumor specificity may well depend on differences between some—as yet unknown—cell membrane property of cells grown in culture and cells growing in tissues of animals, a subject for further investigations. This apparent permeability difference to DIME between cells (both tumor and nontumor) grown in cell cultures and cells operating in vivo does not hold for tumor cells growing in vivo, Kun et al., 1996, "Induction of tumor apoptosis by methyl-3,5-diiodo-4-(4'-methoxyphenoxy) benzoate (DIME)", Abstract No. 102, Int. J. Oncol. 9:supplement 829, because in vivo are killed by DIME feeding, Kun et al., 1996, "Induction of tumor apoptosis by methyl-3,5-diiodo-4-(4'1-methoxyphenoxy) benzoate (DIME)", Abstract No. 102, Int. J. Oncol. 9:supplement 829, The doses of DIME given in vivo (0.25–1.0 g/kg) greatly exceed the extracellular tumoricidal concentration obtained with cell cultures (0.5–2.0 $\mu$M) illustrating that tumor cells in vivo may take up a small portion of the in vivo administered DIME and tumor cells growing in vivo appear to have retained the same sensitivity to DIME as in cell cultures, i.e., tumor cells in culture and in vivo exhibit similar drug uptake. The resemblance of tumor cell membranes in vivo to cell lines growing in cell cultures appears to be a novel propensity of tumor cells, which requires further analysis. In addition to the apparent in vivo selectivity for DIME permeation in tumors, tumor cells differ from normal cells having generally no detectable DIME-esterase activity (not shown), except in the case of A-549 cells (lung cancer). Studies on these cells (FIGS. 4,5) strikingly illustrate that DIME itself, not its esterase-generated metabolite, is the tumoricidal molecule. As seen from Table 8, replacement of the methyl-ester group of DIME (R$_2$) by the longer chain ethyl-ester or by amide groups still sustains considerable antitumor efficacy of certain DIME analogs on E-ras 20 cells. In this study only DIME has been analyzed in some detail, but various "active" DIME analogs also serve further attention, since it is possible that these may have cellular and in vivo effects that can be exploited for additional chemotherapeutic usage. As regards the iodine atoms in DIME and its analogs, these bulky atoms undoubtedly impose conformational constraints between the two benzene rings and at the same time may be critical determinants in cell permeation.

EXAMPLE 10

Action of DIME on Cellular and Nuclear Morphology

The following provides further evidence regarding the broader concept of using thyroxine analogues in treating a wide range of cancers. We have reported that DIME is a powerful inducer of cell death in tumor cells in cell cultures and in vivo. The selective turmoricidal action is most likely explained by selective permeation of this drug, into tumor cells in vivo, Mendeleyev et al., 1997, "Structural Specificity and Tumoricidal Action of Methyl-3,5-Diiodo-4-(4'-Methoxyphenoxy) Benzoate (DIME)," *Intl. J. Oncol.,* in press. As described here, exposure of tumor cells to 1 to 4 DIME results in cytological alterations and a mitotic block predicting the involvement of several biochemical sites of action of DIME. It was of importance to define first the cellular mode of action of DIME by cytometric methods, prior to the analysis of sites at a biochemical level. The present example is concerned with the action of DIME on cell and nuclear morphology and progression through mitosis.

10.1 Microscopic Morphology

Microscopic morphology of E-ras cells was examined by techniques reported earlier, Mendeleyev et al., 1997, "Structural Specificity and Tumoricidal Action of Methyl-3,5-Diiodo-4-(4'- Methoxyphenoxy) Benzoate (DIME)," *Intl. J. Oncol.,* in press; Bauer et al., 1996, "Modification of Growth Related Enzymatic Pathways and Apparent Loss of Tumorigenicity of a ras-Transformed Bovine Endothelial Cell Line" by Treatment With 5-iodo-6-amino-1,2-benzopyrone (INH BP).

10.2 Preparation for M Phase Visualization.

The MDA-MB-231 cell line was obtained from ATCC (Rockville, Md., USA) and cells were cultured in T-75 flasks at 37° C. in Minimum Essential Medium-alpha, supplemented with 10% FCS. In controls, not receiving DIME, 0.1 µg/ml colcemid was added to cultures for 4 hrs prior to the collection of metaphase-blocked cells and preparation of cell spreads. The effects of DIME and colcemid are indistinguishable with respect to the cell cycle block in M phase, therefore when the effects of DIME were tested on metaphase spreads no colcemid was added. Cells ($10^7$) were isolated from T-75 trypsinization for 5 min with 0.025% trypsin, and sedimented by centrifugation, resuspended and kept in 10 ml of 75 mM KCl at 37° C. for 10 min, resedimented, and fixed in 10 ml methanol-acetic acid, with four successive changes of methanol-acetic acid. An aliquot of the final cell suspension (100 µl) was dropped on ethanol-cleaned slides and air-dried.

10.3 In Situ Hybridization.

Human chromosome-specific probes were produced by ONCOR (Gaithersburg, Md., USA). Hybridization was accomplished by a modification of the procedure described by Pinkel et al., 1986, "Cytogentic Analysis Using Quantitative High-Sensitivity Fluorescence Hybridization," *Proc. Natl. Acad. Sci. U.S.A.* 83:2934–2938. The slide-mounted cells were treated with pepsin (20 µg/ml in 0.01 N HCl) at 37° C. for 10 min and then dehydrated in a 70%, 85% and 100% ethanol series, then DNA was denatured by immersion in 70% formamide, followed by 2X standard saline citrate (IX SSC is 0.5 M NaCl, 0.015 M sodium citrate, pH 7.0) for 2 min. at 70° C., and dehydrated in ethanol as described above. The hybridization mixture in a 10 µl total volume consisted of 50% formamide, 2X SSC, 10% dextran sulfate, 0.5 µg herring sperm DNA, and 1–5 µg of proteinase K-treated human placental DNA. Both herring sperm DNA and human placental DNA were previously sonicated to 200–600 bp fragments, and ~40 ng of digoxigeninylated probe DNA (denatured at 70° C. for 5 min) added, and incubated at 37° C. for 1 hr. This mixture was placed on slides containing the fixed cells, sealed under a coverslip, and incubated at 37° C. for 2 to 3 days. After completion of hybridization, the slides were washed in three changes (3×5 min.) of 50% formamide, 2 X SSC, pH 7.0, and twice in PN buffer (consisting of a mixture of 0.1 M NaH2PO4 and 0.1 M NaHP04, 0.1% Nonidet P-40, pH 8.0) at 45° C., then treated with 5 µg/ml antidigoxigenin FITC, 2µg/ml rabbit anti sheep FITC (Boehringer Mannheim), in PNM buffer, (which is 5% non-fat dry milk containing 0.02% sodium azide, after centrifugation to remove solids) for 20 min at room temperature, washed twice for 3 min in PN buffer after each incubation, and stained for DNA with 0.4 µM D API (4,6-diamino-2-phenylindole) in antifade solution (Vector labs, Burlingame, Calif., USA). The slides were viewed in a Zeiss fluorescence microscope equipped with a multiple band pass filter (Chroma Technology, Brattleboro, Vt., USA) to determine the number of FISH signals in each nucleus.

10.4 Time-Lapse Videomicroscopy.

Cells in sealed T-25 tissue culture flasks were placed into a temperature-controlled incubation chamber built to enclose an inverted phase-contrast microscope. The chamber was shielded from ambient room light. Every 5 min, the microscope light was switched on for 12s, during which time an image was captured by an imaging system obtained from Compix, Inc. (Mars, Pa., USA). Image sequences were analyzed with software from the same company.

10.5 Flow Cytometry

Cells exposed to different treatments were grown to confluence, trypsinized, and washed with phosphate buffered saline (PBS). For nuclear analysis, cells were fixed in Vindelov Citrate cell buffer: sucrose 250 mM, trisodium citrate. 2H20 40 mM, DMSO 50 ml in 1000 ml solution, pH 7.6. Normal human lymphocytes obtained from blood were used as controls. Each cell sample and control was counted with a hemacytometer and the cell concentration was adjusted to $2 \times 10^6$ cells/ml. Two million cells from each cell line in a total volume of 2 ml were washed twice with fresh PBS, treated with 200 µg/ml RNAase at 37° C. for 30 min, and stained with 10 µg/ml propidium iodide for 45 min. Flow cytometric analysis was performed on a FACScan benchtop flow cytometer (Becton-Dickinson, San Jose, Calif., USA) equipped with an air-cooled argon laser tuned to 488 nm. Twenty thousand events were collected as six parameter list mode data for analysis and archival storage. Two light scatter parameters (forward and side), propidium iodide fluorescence measured at 575/26 nm and above 620 nm, and doublet discrimination by fluorescence pulse width and area were acquired at 1024 data channel resolution. Acquisition threshold was set on propidium iodide positive events above channel 100. Gating to exclude small debris, large clumps and cell doublets was done post acquisition.

10.6 Immunocytochemistry

Cells were fixed in methanol at −20° C. for 5 min. The primary antibody was mouse monoclonal anti-beta tubulin (Amersham) and secondary antibody from goat, conjugated to fluorescein isothiocyanate from Cappel (Durham, N.C., USA). The DNA of nuclei was stained by 10 min of incubation in 0.05 µg/ml 4'-6-diamidono-2-phenylindole (DAPI). Stained cells were viewed with either a Zeiss 40xPlan-Neofluar or a Nikon 60xPlanApo objective. For classification of cells in the mitotic phase, prophase and metaphase were combined into a single category, because it was difficult to distinguish late prophase from metaphase.

10.7 Results

Figure 10A:
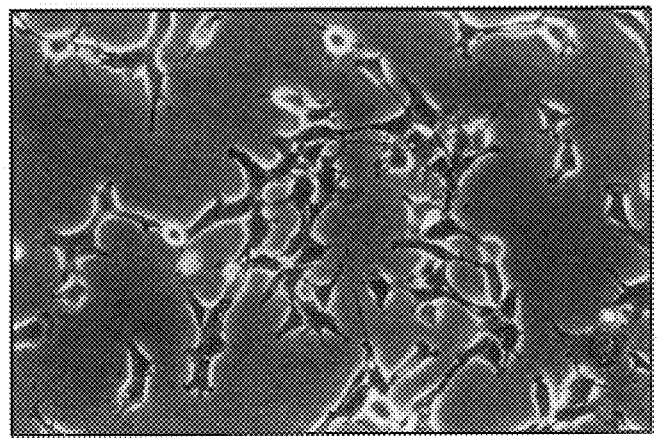
FIG. 10 illustrates the effects on cell morphology following incubation on E-ras 20 cells with 4 μM DIME for 18–24 hours. Panel A, non-drug treated (control); Panel B, drug-treated; Panel C, drug treated. Panels A and B are magnified 150x; Panel C is magnified 300x.
Figure 10B:
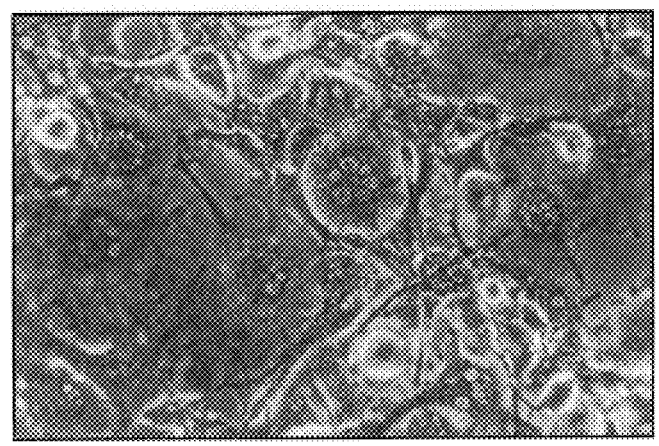
Figure 10C:
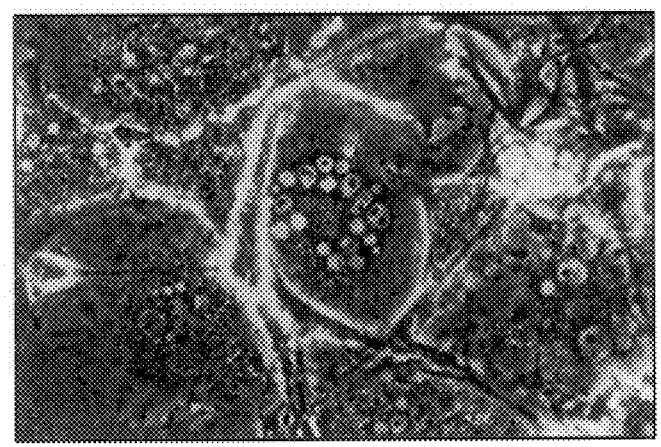
Figure 11A:
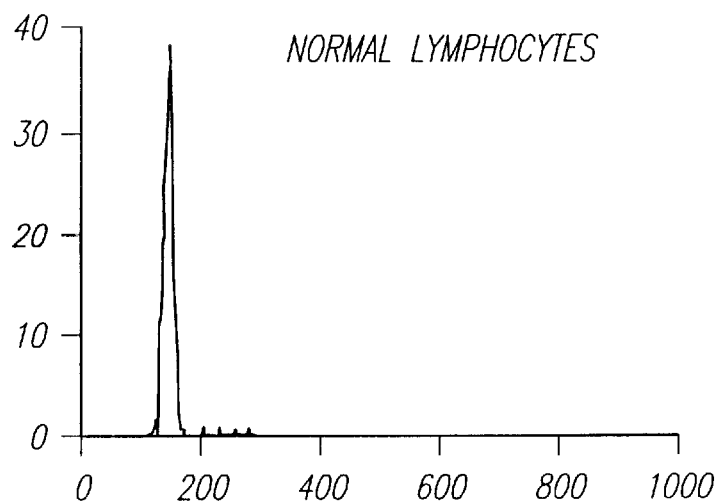
FIG. 11 provides flow cytometric analysis performed on MDA-MB 231 human mammary carcinoma cell nuclei, which demonstrates that by 18 hours of drug exposure, nuclei with a G2 content of DNA had accumulated, indicating M phase block.
Figure 11B:
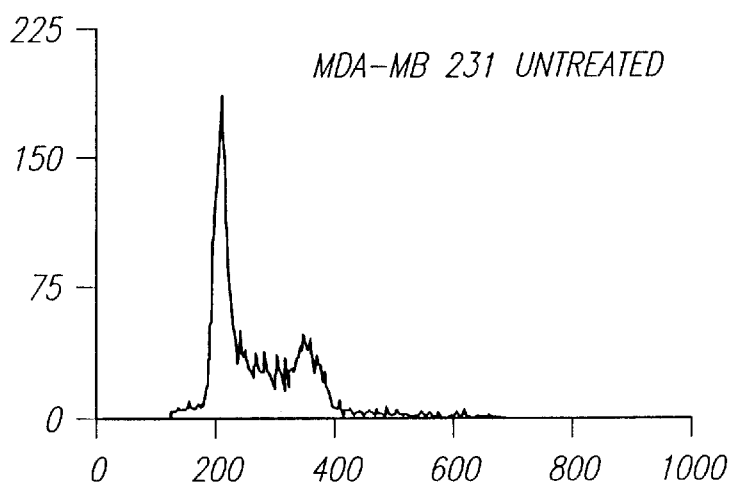
Figure 11C:
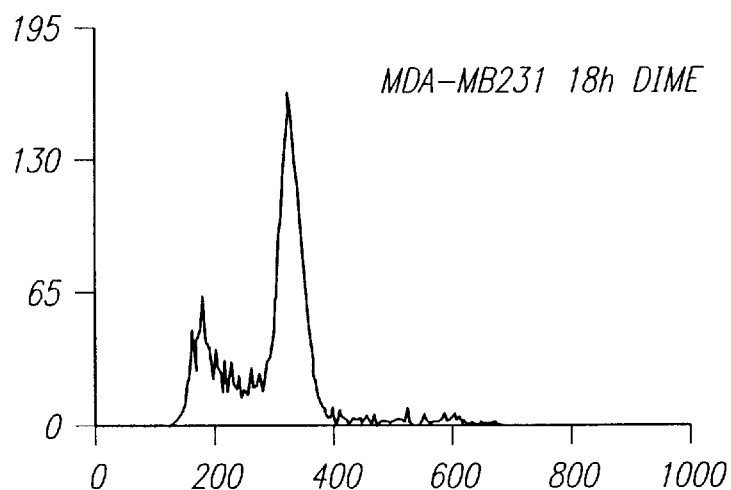

The effects on cell morphology following incubation of E-ras 20 cells with 4 µM DIME for 18–24 hrs are illustrated in FIG. 10. The tumor cells enlarged and, as especially visible at 300-fold magnification, numerous micronuclei appeared. The nature of these cytologic changes was further investigated. Flow cytometric analysis (FIG. 11) performed on MDA-MB 231 human mammary carcinoma cell nuclei demonstrated that by 18 hrs of drug exposure, nuclei with a G2 content of DNA had accumulated, indicating M phase block.

Figure 12:
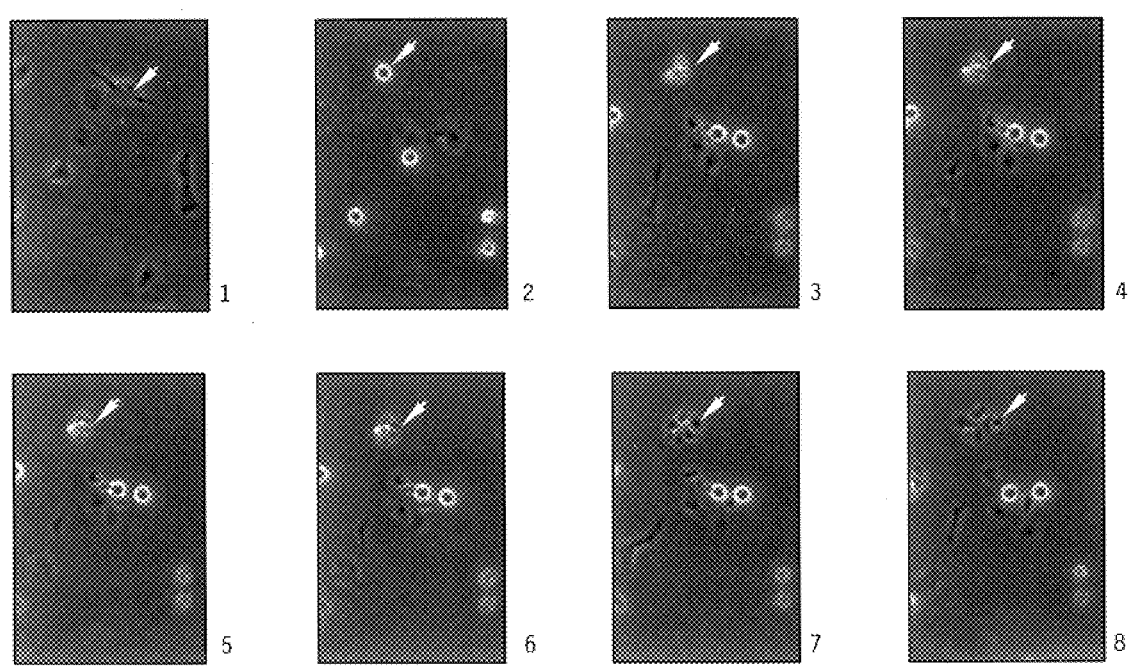
FIG. 12 shows images which illustrate a 13 hour delay in mitosis followed by irregular division into six daughter cells. Frame 1, 0 hr.:0 min.; Frame 2, 10:55; Frame 3, 24:20; Frame 4, 24:40; Frame 5, 24:55; Frame 6, 25:10; Frame 7, 26:35; Frame 8, 28:20.

The above observation prompted us to examine the kinetics of entry into mitosis in cells exposed to DIME. Cells were incubated in medium containing I µM DIME and followed by time-lapse videomicroscopy as described in Materials and Methods. FIG. 12 shows images which illustrate a 13 hr. delay in mitosis followed by irregular division into 6 daughter cells. In contrast, control cells delayed approximately 0.5 hr in mitosis (see FIG. 13) and always divided to yield exactly 2 daughter cells (data not shown).

Time-lapse videomicroscopy also enabled us to monitor the fates of the daughter cells resulting from the irregular cell division described above. Twenty percent of the mitosis viewed in the presence of 1 µM DIME yielded daughter cells which fused (Table 12), often yielding large multinucleated cells of the type seen in FIG. 10. Control cells did not exhibit such division followed by fusion.

TABLE 12

DIME includes fusion between daughter cells following mitosis

| | No. of mitoses monitored[a] | No. of mitosis followed by fusion of daughter cells[b] |
|---|---|---|
| 1.0 µM DIME | 35 | 7 |
| Control | 32 | 0 |

[a]Mitoses were monitored by time-lapse videomicroscopy during continuous exposure of cells to DIME;
[b]Fusion of daughter cells usually occurred within minutes of cytokinesis and involved 2–5 daughter cells.

Figure 14:
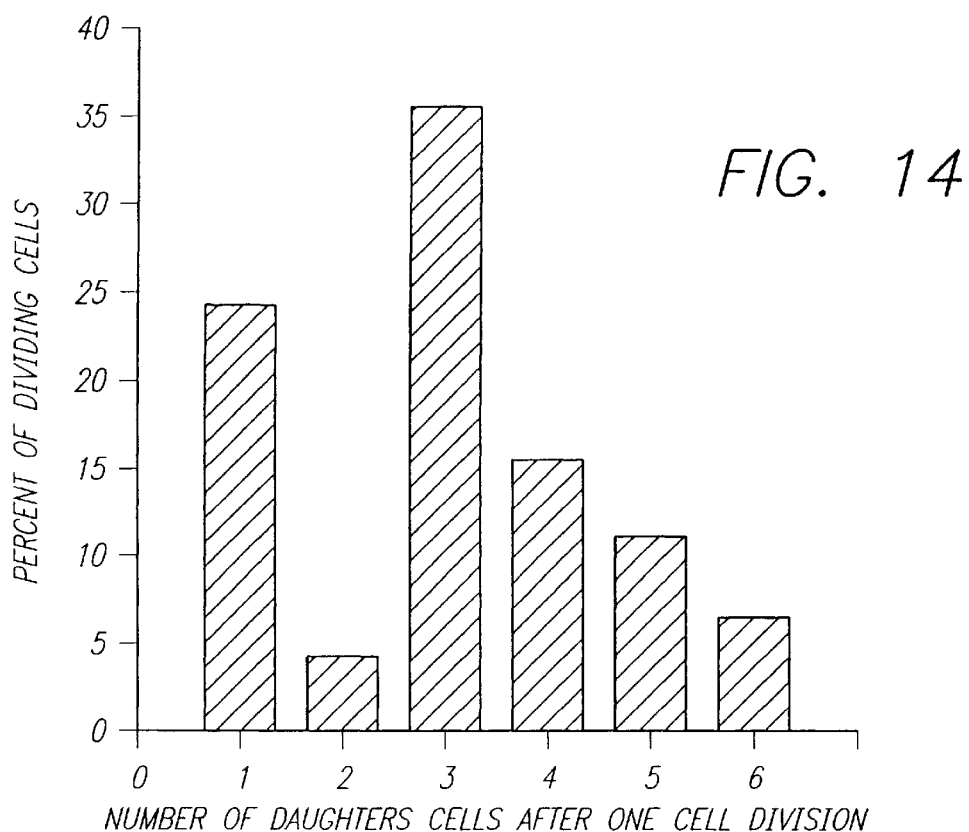
FIG. 14 shows the quantitative analysis of the abnormal cell division induced by DIME.

The cell division which took place in the presence of 1 µM DIME was examined to quantitatively assess the number of daughter cells resulting from each mitosis (FIG. 14). The number of daughter cells ranged from 1 to 6 per mitotic event. In contrast control cells always (33/33) divided to yield 2 daughters. Thus the drug-induced long delay in mitosis described above was followed by a highly abnormal pattern of cell division.

Figure 13:
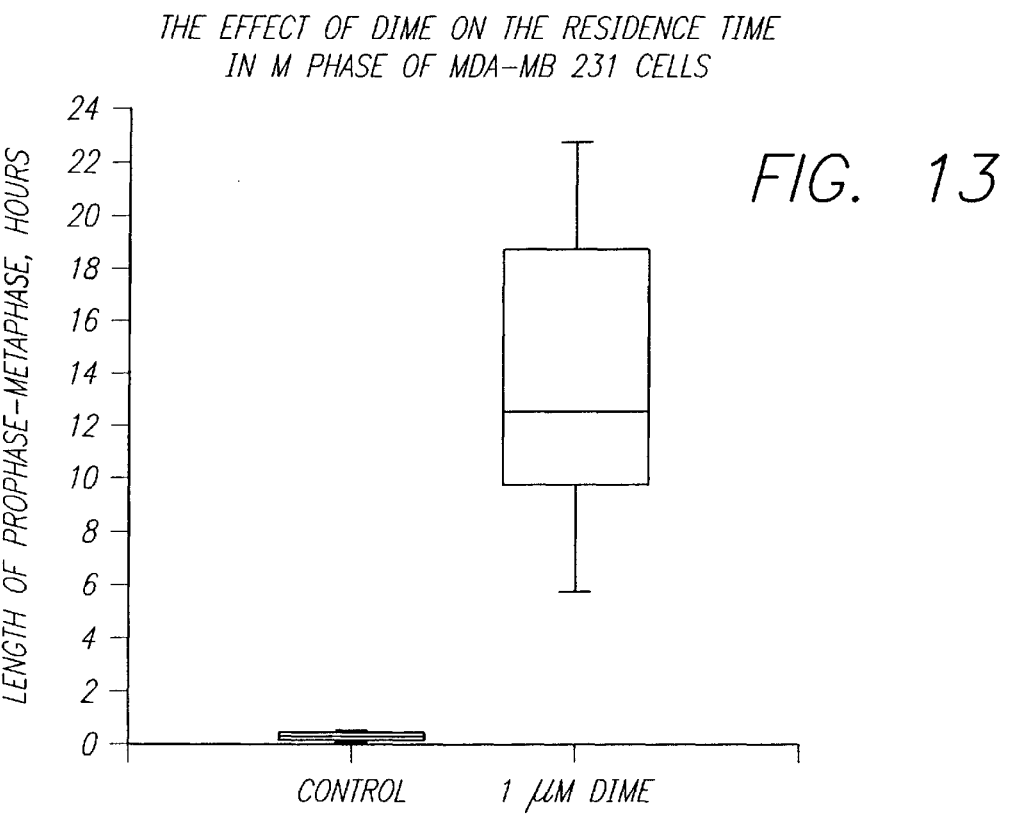
FIG. 13 shows the effect of DIME on the residence time in M phase of MDA-MB-231 cells.
Figure 15:
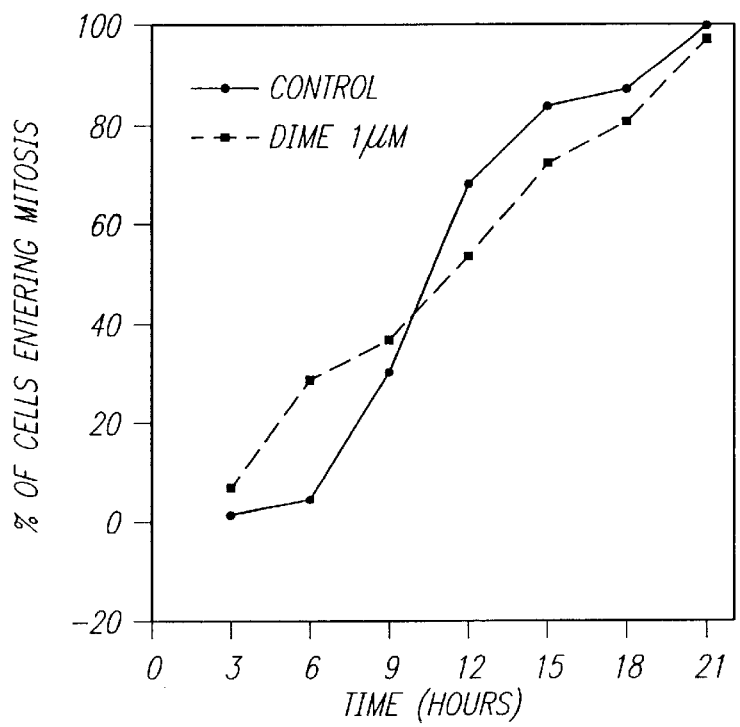
FIG. 15 shows the effect of DIME on the rate of entry into M phase of MDA-MB-231 cells.

FIG. 15 shows the rates at which cells incubating in 1 µM DIME and control cells entered mitosis. The curves are nearly coincident, indicating that DIME did not affect the rate at which the cells traversed interphase. In contrast, the average period of time each cell spent in mitosis was increased more than 20-fold by the drug (FIG. 13). That the cells blocked by DIME in a rounded configuration really were in mitosis was confirmed by their condensed and enlarged chromatin (FIG. 16) and abnormal mitotic spindles (FIG. 17).

Figure 16A:
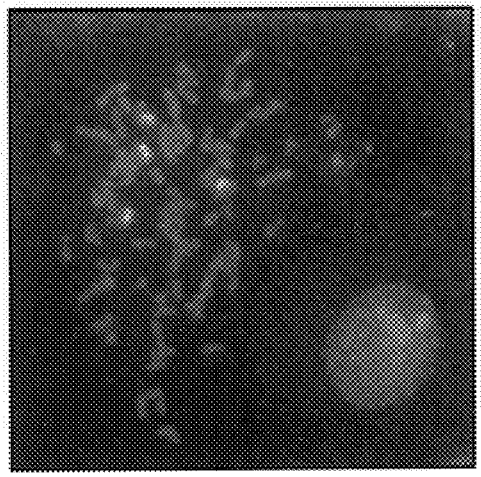
FIG. 16A is the control.
Figure 16B:
FIG. 16B is the DNA stained image.
Figure 16C:
FIG. 16C is the hybridization of chromosome 19 of the 1 μM DIME treatment for 5 days (metaphase).

Chromosome analyses by in situ hybridization of metaphase nuclei were performed with probes specific for chromosomes 1, 2, 7, 11 and 19. They all yielded similar results, therefore only chromosome 19 is illustrated. Representative results are shown for chromosome 19 in FIGS. 16 A,B and C. In all cases MDA-MB-231 (human mammary cancer) cells were used. FIG. 16A shows in situ hybridization on chromosome 19. Exposure to 1 µM DIME for 18 hrs had no detectable effect, therefore FIGS. 16A and 16B represent both control and drug-treated cells. FIG. 16B is DNA staining (DAPI) illustrating the coincidence of DNA staining, with chromatin whereas FIG. 16A is stained for chromosome 19. However, drug exposure of cells (1 µM DIME) for 5 days induces a large accumulation of metaphase chromatin in some cells, with about 40 chromosome-19 signals, and over 100 chromosomes (FIG. 16C). No evidence for chromosome breakage could be obtained, even though this drug treatment eventually kills cells, Mendeleyev et al., 1997, "Structural Specificity and Tumoricidal Action of Methyl-3,5-Diiodo-4-( 4'-Methoxyphenoxy) Benzoate (DIME)," *Intl. J. Oncol.* 10:689–695.

Figure 17A:
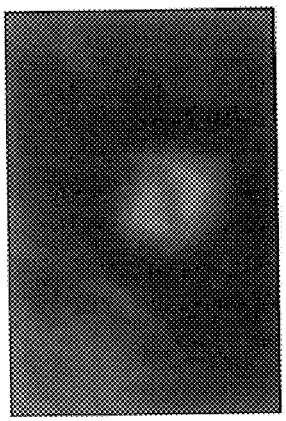
FIGS. 17 (A, B and C) shows the effect of DIME treatment on mitiotic spindle of MDA-MB-231 cells. Panel A, control (no drug); Panel B, 1 μM DIME for 18 hrs.; Panel C, 1 μM DIME for 5 days.
Figure 17B:
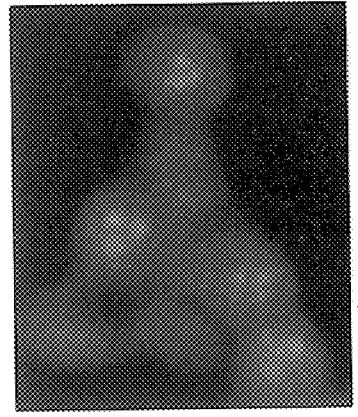
Figure 17C:
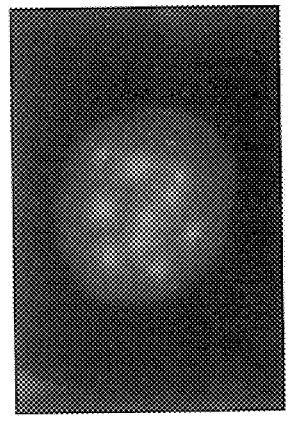
Figure 19:
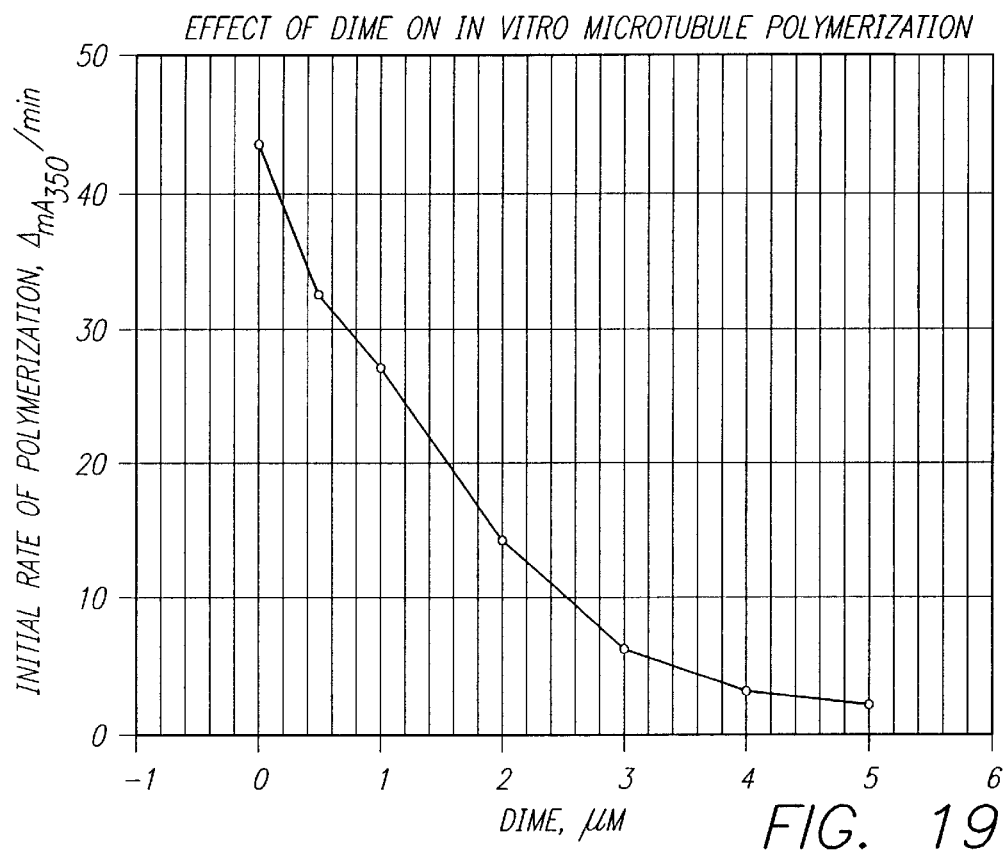
FIG. 19 shows the effect of increasing concentration of DIME on the initial linear rate of MTP polymerization. The concentration of GTP was 1 mM, other conditions were identical with those given in the legend of Table 13.

The structure of the mitotic spindle following 18 hrs exposure to 1 µM DIME is depicted in FIG. 17. FIG. 17A is the tubulin-stained mitotic spindle in non-drug treated MDA-MB-231 cancer cells. FIG. 17B shows changes after 18 hrs drug exposure which consisted of striking abnormalities of-tubulin distribution. These multicentric structures were even more exaggerated after exposure to 1 µm DIME for 5 days (FIG. 17C). The cellular multicentric distribution of tubulin (FIGS. 17B and 17C) appears similar to the nucleation of tubulin by added centrosomes in vitro as shown by Mitchison et al., 1984, "Microtubule Assembly Nucleated by Isolated Centrosomes" *Nature* 312:232–237. However we were unable to detect abnormal number of centrosomes by immunofluorescence (data not shown), thus the apparent multicentric nucleation of tubulin following 18 hrs DIME (1 µM) treatment may not be directly related to centrosomes. These pictures do not predict whether or not 1 µM DIME induces tubulin depolymerization or inhibits repolymerization.

In preliminary studies (data not shown) we have also studied the behavior of certain spindle-associated proteins by the immunocytologic technique. Cdc-2 kinase was not associated with the spindle in the absence of 1 µM DIME, but exposure of cells to the drug, for 18 hrs demonstrated induction of cdc-2-kinase-spindle binding. Drug treatment did not alter the pattern of staining by antiserum to the centrosomal protein pericentrin, since only two foci were seen. Cyclin B-microtubule-spindle association also remained unchanged. However, the drug induced abnormal organization of the spindle pole centers still bound cyclin B. Protein phosphatase 2a (pp2a)-spindle association, just like that of pericentrin or cyclin B, was not influenced by drug-treatment (1 µn for 18 hrs).

These exploratory studies comprise the basis of further cell biological research. In preliminary experiments the possible role of phosphatases in the protein-spindle associations was also tested. Exposure to 100 nM extracellularly added okadaic acid for 18 hrs abolished only cdc-2 kinase- and pp2a-spindle association, suggesting the involvement of protein phosphatases (data not shown).

These results appear to discriminate between early effects of IµM DIME, which take place within 18–24 hours after drug exposure, and late consequences seen here in chromosome numbers that develop after 5 days of drug treatment. However, it is probable that late events merely reflect a cascade of cellular reactions initiated by the binding of DIME to certain cellular sites. Early events include marked cytologic changes, specifically the appearance of large multinucleated cells. Formation of micronuclei is well known to occur after radiation injury, which consists of the failure of acentric chromosome fragments to undergo nuclear migration to poles during anaphase due to the absence of kinetochores and microtubule spindle attachment, Bedford, J. S., 1991, "Sublethal Damage, Potentially Lethal Damage, and Chromosomal Aberration in Mammalian Cells Exposed to Ionizing Radiation," *J. Radiation Oncol. Biol. Phys.* 21:1457–1469. Time lapse studies have shown that vinblastine sulfate also induces metaphase blocked multinucleated cells, Kirshan, 1968, "Time Lapse and Ultrastructure Studies on the Reversal of Mitotic Arrest Induces by Vinblastine Sulfate in Earl's L Cells," *J. Natl. Cancer Institute* 41:581–595, reminiscent of results shown here (FIG. 10), except vinca alkaloids also exhibit severe toxic effects in animals while DIME does not. over expression of protein phosphatase 2a (pp2a) also induces multinucleation, Wera et al., 1995, "Deregulation of Transitional Control of the 65 kDa Regulatory Subunit (PR65 Alpha) of Protein Phosphatase 2A leads to Multinucleated Cells," *J. Biol. Chem.* 270:21374–21381, clearly indicating that the mechanism of development of this complex process (multinucleation) may involve a variety of probably connected enzymatic activities. These results show an activation of pp2a in DIME cells (l.c.1), an effect which is probably due to a direct action of DIME on this enzyme. The participation of various cellular enzymes in the mode of action of DIME is the subject of a separate biochemical report.

One of the most readily observable cellular phenomena induced by DIME is a blockade in M phase (FIGS. 11 and 13), very similar to the action of colcemid or especially vinca alkaloids, which can be replaced by DIME. Late effects (5-days) of DIME, as illustrated by DNA-fluorescence hybridization with probes to chromosomes 1, 2, 7, 11 and 19, are the result of a accumulation of chromosomes, due to the failure of cell division. DIME has no apparent direct effect on DNA. The cuts in double-stranded DNA (FIG. 12 in Mendeleyev et al., 1997, "Structural specificity and tumoricidal action of methyl-3,5-diiodo-4-(4'-methoxyphenoxy) benzoate (DIME)" *Int. J. Oncology* 10:689–695, are downstream consequences of the interaction of DINE with cancer cells and most probably reflect the upregulation of DNA endonucleases that are de-poly-ADP-ribosylated in DIME-treated cells by way of an indirect activation of poly(ADP-ribose) glycohydrolase (footnote I in ref 1). Endonuclease activation may not be the only single provocation of programmed cell death by DIME, since it is known that diverse molecular mechanisms can lead to apoptosis Wertz et al., 1996, "Diverse Molecular Provocation of Programmed Cell Death," *TIBS* 21:359–364. Development of an abnormal mitotic spindle in DIME-treated cells points to an initiating cellular action of DIME on the tubulin system, that is well known to play a pivotal role in cytokinesis, Murray et al., 1993, "The Cell Cycle: An Introduction.," *Oxford University Press, New York*.

Since DIME is a "hormonally inactive" thyroid hormone analog the intriguing question arises whether or not metabolic precursors (or catabolytes) of thyroid hormones may play a role in physiologic differentiation maintenance, serving as "antimalignancy" proof reading regulators. A search for thyroid hormone metabolites with tumoricidal action appears warranted.

EXAMPLE 11

Effect on Tubulin Polymerization

In the following experiments the hormonally inactive thyroid hormone analog, DIME, at 1 to 5 $\mu$M concentrations inhibits the GTP-dependent polymerization of MTP as determined by an optical test. This inhibition is critically dependent on the concentration of GTP. The quantitative correlation between the concentrations of DIME and GTP, under conditions of a linear rate of MTP polymerization, follows Michaelis-Menten kinetics and the inhibition portrays a "mixed" type, where $k_m$ for GTP and $U_{max}$ are altered simultaneously. Chemical analogues of DIME inhibit MTP polymerization parallel to their antitumorigenic action in vivo. The MTP site is one of the early cellular response sites of DIME.

Exposure of human mammary cancer cells (MDA-MB-231) to 1 $\mu$M DIME induced abnormal spindle structures within 18 hours of drug treatment, thus a putative DIME-microtubule-protein (MTP) interaction appears to be a component of early cellular responses to the drug, Zhen, et al., 1997, "Cellular Analysis of the mode of action of methyl-3–5-diiodo-4-(4'-methoxyphenoxy) benzoate (DIME) on tumor cells", *Intl. J. Oncol.* Abnormal spindle structures could be the result of DIME-MTP interaction or reactions of DIME with components of the microtubule organizing center or with as yet undefined systems sequentially or in concert. Since time-dependent quantitative analysis of the MTP system in situ is unsuitable for initial velocity measurement we adapted the in vitro assembly system of neurotubules as a model for a quantitative analysis of the interaction of DIME with MTP. As demonstrated by, Gaskin , et al., 1974, "Turbidimetric studies of the in vitro assembly and disassembly of porcine neurotubules", *J. Mol. Biol.* 89:737–758; and Kirschner, et al., 1974, "Microtubules from mammalian brain: some properties of their depolymerization products and a proposed mechanism of assembly and disassembly", *Proc. Natl. Acad. Sci. U.S.A.* 71:1159–1163; this system is suitable for kinetic assay of MTP assembly in vitro. The time course of MTP assembly consists of initiation and propagation and termination steps, Gaskin, et al., 1974, "Turbidimetric studies of the in vitro assembly and disassembly of porcine neurotubules", *J. Mol. Biol.* 89:737–758. The rate of propagation under defined conditions is sufficiently linear to permit kinetic analysis, that can be evaluated with respect DIME and GTP concentrations. As we show here the inhibition of MTP assembly by DIME occurs in the same range of drug concentration as required to inhibit tumorigenesis in vivo, or to inhibit cell replication or induce eventual cell death; Mendeleyev, et al., 1997. "Structural specificity and tumoricidal action of methyl-3, 5-diiodo-4-(4'-methoxyphenoxy) benzoate (DIME)" *Int. J. Oncol.*, 10:689–695 and Table 8, above; therefore the DIME-MTP interaction is most probably a component of the apparently pleiotropic cellular mechanism of action of DIME.

11.1 Isolation of Microtubule Proteins (MTP).

Preparation of MTP and an optical test for polymerization was adopted from published methods, Gaskin, et al., 1974, "Turbidimetric studies of the in vitro assembly and disassembly of porcine neurotubules", *J. Mol. Biol.* 89:737–758;

Tiwari, et al., 1993, "A pH and temperature-dependent cycling method that doubles the yield of microtubule protein", *Anal. Biochem.* 215:96–103. Bovine or rabbit brain was homogenized in an equal volume of ice cold buffer containing 100 mM Pipes/K+(pH 7.4), 4 mM EGTA, 1 mM $MgCl_2$, 0.5 mM DTT and 0.1 mM PMSF, and centrifuged at 39,000 g for 1 hour at 4° C. To the supernatant, DMSO (8% final concentration) and GTP (1 mM final concentration) were added, followed by incubation at 37° C. for 30 minutes. Microtubules were pelleted at 100,000 g at 37° C for 30 minutes. The pellets were incubated on ice for 15 minutes, followed by resuspension in ice cold PEM buffer (100 mM Pipes/K+(pH 6.9), 1 mM EGTA, 1 mM $MgCl_2$). This warm polymerization and cold depolymerization cycle was repeated once more and the cold, resuspended monomeric MTP (8–10 mg/ml protein) was used for the optical test for polymerization kinetics. Both rabbit or bovine brain yielded identical MTP preparations.

The composition of the optical test is described in the legends of Figures and Table 12. The polymerization reaction was started by the addition of 100 μl of MTP solution (equivalent to 0.8–1.0 mg protein) and initial linear rates of increase in absorbance at 350 nm followed and recorded at 37° C. (see FIG. 1) in a Perkin-Elmer 552 double beam spectrophotometer, equipped with a thermostatically controlled cuvette holder.

11.2 Results and Discussion

Figure 18:
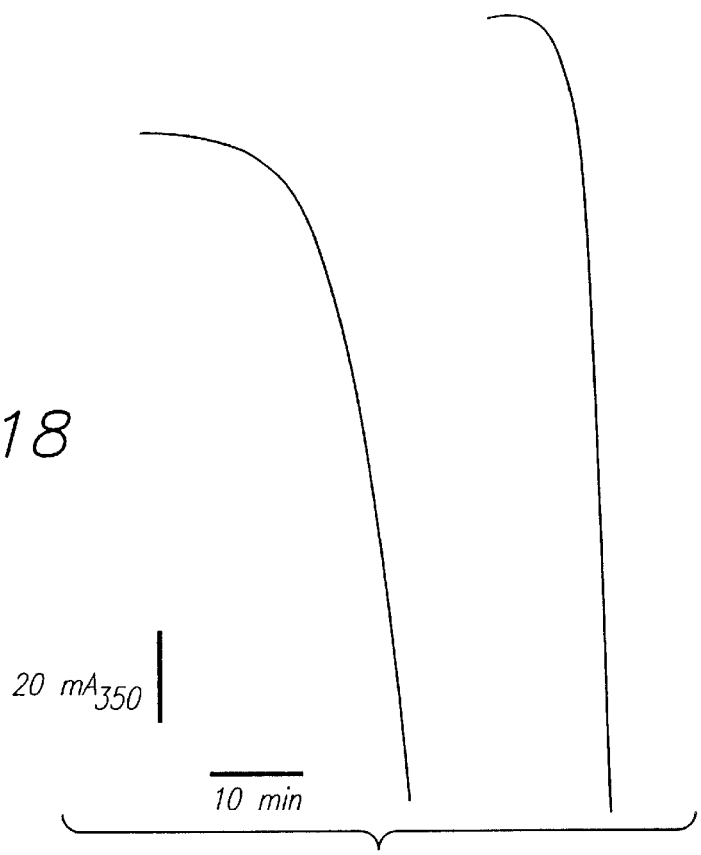
FIG. 18 shows an optical test for microtuble assembly (MTP polymerization). The concentration of GTP was 1 μM (right curve) and the effect of 4 μM DIME is illustrated in the left curve. Other conditions were the same as described in the legend of Table 13.

The precision of the optical assay for the polymerization of MTP is illustrated in FIG. 18. Experimental conditions were the same as given in the legend of Table 7 except GTP concentration was 1 mM (right curve) and DIME was present at 4 μM (left curve) It is apparent that the rate of MTP polymerization proceeds in a linear manner, thus conditions for maximal polymerization rates as defined by Berne, B, 1974, "Interpretation of light scattering from long rods", *J. Mol. Biol.* 89:755–758 appear fulfilled. Therefore it is possible to determine the quantitative correlation between [DIME] and [GTP] by comparing the linear rate in the presence of varying drug and activator concentrations. At 1 mM GTP concentration, increasing concentrations of DIME progressively inhibit MTP polymerization (FIG. 18).

Figure 20:
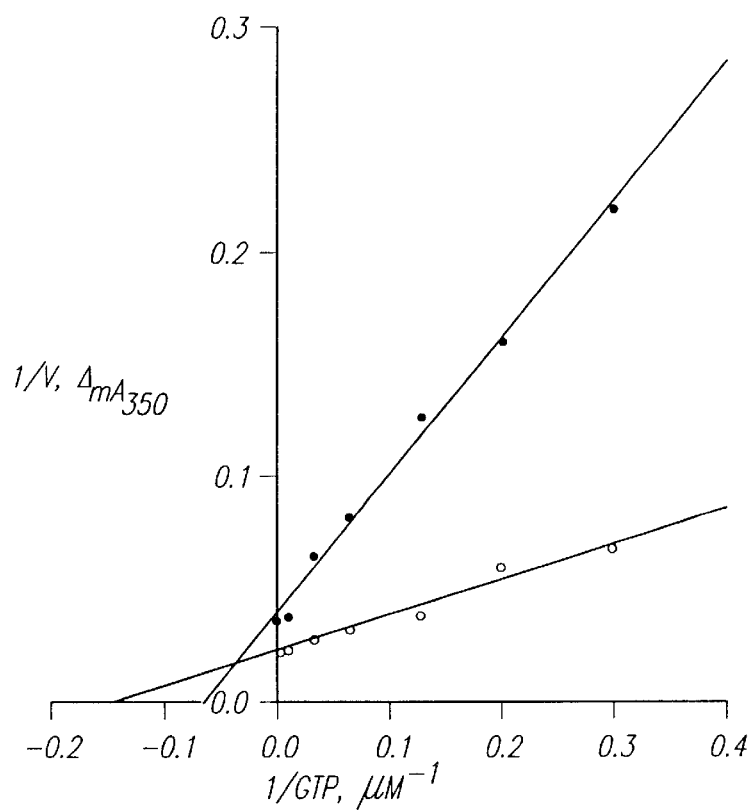
FIG. 20 shows the Michaelis-Menten analysis of the effect of 1 μM DIME (closed circles) on the initial linear rate of MTP polymerization as a function of GTP concentration (open circles, no drug). Other conditions were the same as described in the legend in Table 13.

As shown in FIG. 20, inhibition of 1 μM DIME quantitatively correlated with [GTP] and a double reciprocal plot produced a "mixed" type inhibition, Dixon, et al., 1964 *Enzymes*, pp. 234–237, Acad. Press, Inc., New York. Both $V_{max}$ and $k_m$ values were changed by nearly 50% km GTP from 6.7 μM to 14 μM, while $V_{max}$ decreased by close to 50%. The simplest interpretation of a mixed inhibition, based on the Briggs-Haldane equation (cf. 7) is that $k_2$, i.e., the dissociation [ES] to E and P (product), is directly affected which then modifies both $k_m$ and $V_{max}$. The exact nature of $k_2$ is presently unknown and its determination requires analysis of reaction products of GTP hydrolysis, a work to be reported elsewhere. Allosteric modifications may also accomplish similar results, Dixon, et al., 1964 *Enzymes*, pp. 234–237, Acad. Press, Inc., New York. The purpose of the present experiments is to compare the effectivity of DIME with some of its analogues on MTP polymerization (see Table 12) and correlate results with cytophathologic processes (e.g., inhibition of tumorigenesis in vivo).

There is apparent correlation between the chemical structure of DIME and 7 of its analogues that an act on MTP polymerization (Table 13) and their inhibitory potency on in vivo tumorigenesis (compare with Table 8 or Mendeleyev et al. supra). For example substitution $R_1$ from $CH_3O$ to EtO and n-BuO progressively diminishes inhibition of MTP polymerization, almost exactly parallel to the decreasing antitumorigenic effect (compare with Table 8 or or Mendeleyev et al. suPra). On the other hand, substitution in $R_2$ from the methyl ester to the carboxylic acid completely abolishes the inhibitory effect on MTP polymerization but only halves the antitumorigenic action, tested with E-ras 20 cells (see Table 8 and FIG. 5 or Mendeleyev et al. supra). It is possible that such quantitative differences may reflect cell type specific variations.

TABLE 13

Effect of DIME and some analogs in microtubule assembly in vitro $$R_1-\bigcirc-O-\bigcirc(I)(I)-C(=O)-R_2$$

| Compound No. | $R_1$ | $R_2$ | Percent inhibition of initial velocity |
|---|---|---|---|
| 1 | $CH_3O$ | $CH_3O$ | 93 |
| 2 | EtO | $CH_3O$ | 76 |
| 4 | n-BuO | $CH_3O$ | 8 |
| 6 | $CH_3O$ | HO | 0 |
| 5 | $CH_3O$ | EtO | 35 |
| 7 | $CH_3O$ | $H_2N$ | 43 |
| 9 | $CH_3O$ | $(CH_3)_2N$ | 6 |
| 18 | $CF_3O$ | $CH_3O$ | 7 |

The assay system consisted of 240 μl of PEM buffer containing 8% DMSO and GTP (final concentration 1 mM), 10 μM final concentration of drug (added in 3 μl), or solvent control and 0.6 mg MTP (60 μl). Microtubule assembly at 37° C. was monitored at λ=350 nm and initial velocities were calculated as $mA_{350}$/min. The control had an initial velocity of 180 $mA_{350}$/min. The values are averages of duplicate assays.

Inhibition of MTP polymerization may have highly complex cellular consequences. In cytokinesis this inhibition may interfere with traction forces of tubulin and prevent the formation of a cleavage furrow which is essential for cell division, Burton, et al., 1997, "Traction forces of cytokinesis measured with optically modified elastic substrate", *Nature* 385:450–454. The inhibition of MTP * - polymerization by DIME should be correlated with the biochemical sites of this drug. As compared with Mendeleyev et al.; supra, DIME directly activates pp2-ase, therefore it is necessary to coordinate this effect with mitosis-related phenomena induced by DIME. For example it was recently reported, Kawabe, et al., 1997, "HOXII interacts with protein phosphatase pp2a and ppl and disrupts G2/M cell cycle check point" *Nature* 385:454–458. that pp2-ase may regulate G2/M transition and pp2-ase is also a potential oncogene, the inhibition of which promotes oncogenesis. It is possible that activation of pp2-ase by DIME be antagonistic to oncogenesis.

On the basis of these experiments, it can be seen that thyroxine type analogues, such as DIME, are capable of blocking mitosis in cancer cells. The present invention provides for a rapid screen for such compounds by use of these techniques and use of cell sorters, chromosome blot or other analysis of DNA in cells.

The foregoing written specification is considered to be sufficient to enable one skilled in the art to practice the invention. Various modifications of the above-described modes for carrying out the invention which are obvious to those skilled in the pharmaceutical arts or related fields are intended to be within the scope of the following claims.

What is claimed is:

1. A method of treating a malignant tumor sensitive to the compounds below, in a mammal, the method comprising administering to said mammal an effective amount of a thyroxine analogue having no significant hormonal activity, in an amount sufficient to depress growth of the malignant tumor, wherein the thyroxine analogue is characterized as being a compound capable of causing about 35 percent or more inhibition of initial velocity of microtubule protein assembly in vitro wherein said thyroxine analogue has the formula:

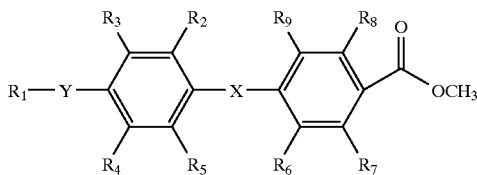

and pharmaceutically acceptable salts thereof, wherein:

$X=O$, S, $CH_2$, carboxy or absent;

$Y=O$ or S;

$R_1$=methyl or ethyl;

$R_2$, $R_3$, $R_4$ and $R_5$ are independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy and halogen; and $R_6$, $R_7$, $R_8$ and $R_9$ are independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$ and $NH_2$.

2. The method according to claim 1, wherein the thyroxine analogue has the formula:

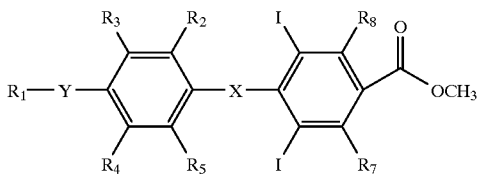

and pharmaceutically acceptable salts thereof, wherein:

$X=O$, S, $CH_2$, carboxy or absent;

$Y=O$ or S;

$R_1$=methyl or ethyl;

$R_2$, $R_3$, $R_4$ and $R_5$ are independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy and halogen; and $R_7$ and $R_8$ are independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$ and $NH_2$.

3. The method according to claim 1, wherein the thyroxine analogue is administered in an amount effective to cause regression of the malignant tumor.

4. The method according to claim 1, wherein the malignant tumor is selected from the group consisting of carcinoma and sarcoma.

5. The method according to claim 1, wherein the thyroxine analogue is administered orally.

6. A method of treating cancer sensitive to the compounds below, the method comprising administering to a mammal having cancer an amount of thyroxine analogue effective to treat cancer, wherein the thyroxine analogue has the structural formula:

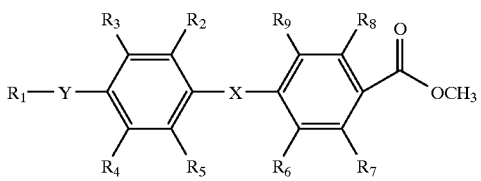

and pharmaceutically acceptable salts thereof, wherein:

$X=O$, S, $CH_2$, carboxy or absent;

$Y=O$ or S;

$R_1$=methyl or ethyl;

$R_2$, $R_3$, $R_4$ and $R_5$ are independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy and halogen; and $R_6$, $R_7$, $R_8$ and $R_9$ are independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$ and $NH_2$.

* * * * *